(12) United States Patent
Guo et al.

(10) Patent No.: US 8,440,641 B2
(45) Date of Patent: *May 14, 2013

(54) PHTHALOCYANINE SALT FORMULATIONS

(75) Inventors: Ming Guo, Cleveland, OH (US); Yun Liu, Cleveland, OH (US); Malcolm E. Kenney, Cleveland Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 175 days.

This patent is subject to a terminal disclaimer.

(21) Appl. No.: 12/408,116

(22) Filed: Mar. 20, 2009

(65) Prior Publication Data

US 2010/0240609 A1   Sep. 23, 2010

(51) Int. Cl.
*A61K 31/695* (2006.01)
*C09B 47/04* (2006.01)

(52) U.S. Cl.
USPC .......................................... 514/63; 540/139

(58) Field of Classification Search ...... 514/63; 540/139
See application file for complete search history.

(56) References Cited

U.S. PATENT DOCUMENTS

| 5,358,940 | A | 10/1994 | Capraro et al. |
| 5,484,778 | A | 1/1996 | Kenney et al. |
| 5,763,602 | A | 6/1998 | Li et al. |
| 6,511,971 | B1 | 1/2003 | Gorun |

FOREIGN PATENT DOCUMENTS

| EP | 0633024 A1 | 1/1995 |
| EP | 0720853 B1 | 7/1996 |
| RU | 2146144 C | 3/2000 |
| WO | 9201753 A1 | 2/1992 |
| WO | 9506688 A1 | 3/1995 |
| WO | 9923882 A1 | 5/1999 |
| WO | 02096913 A1 | 12/2002 |
| WO | 03037902 A1 | 5/2003 |
| WO | 2005099689 A1 | 10/2005 |
| WO | WO2005/099689 | * 10/2005 |

OTHER PUBLICATIONS

Copper et al. CAS: 143:418226, 2005.*
Wainwright, Mark; "Local treatment of viral disease using photodynamic therapy; International Journal of Antimicrobial Agents", vol. 21, (2003), pp. 510-520.
Miller et al., "Photodynamic Therapy with the Phthalocyanine Photosensitizer Pc4: The Case Experience with Preclinical Mechanistic and Early Clinical-Translational Studies"; Toxicol Appl Pharmacol, 224(3) (2007), pp. 290-299.
Ben-Hur et al., "The phthalocyanines: a new class of mammalian cells photosensitizers with a potential for cancer phototherapy"; Int. J. Radiat. Biol., (1985), vol. 47, No. 2, pp. 145-147.
Swick et al., "Successful penetration of topically-applied silicon phthalocyanine photosensitizer Pc 4 and new Pc 4 salts into human skin", Journal of Investigative Dermatology, (2004), vol. 122, Issue 3, p. A146; Abstract only.
Ke et al., "Apoptosis Mechanisms Related to the Increased Sensitivity of Jurkat T-cells vs A431 Epidermoid Cells to Photodynamic Therapy with the Phthalocyanine Pc4", Photochemistry and Photobiology, (2008), vol. 84, pp. 407-414.
Allen et al.; "Current status of phthalocyanines in the photodynamic therapy of cancer", Journal of Porphyrins and Phthalocyanines, (2001), vol. 5, pp. 161-169.
Ben-Hur et al.; "Phthalocyanines in Photobiology and Their Medical Applications", The Porphyrin Handbook, (2003), vol. 19, pp. 1-35.
Abernathey et al.; "Activity of Phthalocyanine Photosensitizers against Human Glioblastoma in Vitro", Neurosurgery, (1987), vol. 21, pp. 468-473.
Chan et al.; "Tissue Uptake, Distribution, and Potency of the Photoactivatable Dye Chloroaluminum Sulfonated Phthalocyanine in Mice Bearing Transplantable Tumors", Cancer Research, (1988), vol. 48, pp. 3040-3044.
Sonoda et al.; "The Role of Singlet Oxygen in The Photohemolysis of Red Blood Cells Sensitized by Phthalocyanine Sulfonates", Photochemistry and Photobiology, (1987), vol. 46, No. 5, pp. 625-631.
Ramakrishnan et al.; "DNA Lesions and DNA Degradation in Mouse Lymphoma L5178Y Cells After Photodynamic Treatment Sensitized by Chloroaluminum Phthalocyanine", Photochemistry and Photobiology, (1989),vol. 50, No. 3, pp. 373-378.
Agarwal et al.; "Photodynamic Therapy Induces Rapid Cell Death by Apoptosis in L5178Y Mouse Lymphoma Cells", Cancer Research, (1991), vol. 51, pp. 5993-5996.
Office Action from U.S. Appl. No. 10/599,433, dated May 16, 2011.
Response to Office Action dated May 16, 2011 from U.S. Appl. No. 10/599,433, submitted Jun. 6, 2011.
Office Action from U.S. Appl. No. 10/599,433, dated Jun. 21, 2011.
Response to Office Action dated Jun. 21, 2011 from U.S. Appl. No. 10/599,433, submitted Sep. 9, 2011.
International Search Report and Written Opinion from International Application No. PCT/US10/27898, date of mailing Apr. 30, 2010.

* cited by examiner

*Primary Examiner* — Rei-tsang Shiao
(74) *Attorney, Agent, or Firm* — Tarolli, Sundheim, Covell & Tummino LLP

(57) ABSTRACT

Pharmaceutical compositions of phthalocyanine compounds with a structure according to Formula (I) are described. Phthalocyanines are photosensitizer compounds having a phthalocyanine ring system that can be used for photodynamic therapy. Different phthalocyanines and phthalocyanine salts are shown to have useful characteristics such as water solubility, oil solubility, or tunable photostability. Formulations of phthalocyanines and phthalocyanine salts that can be used for topical and systemic administration are described.

14 Claims, 9 Drawing Sheets

| | Pc | name | X⁻ | % |
|---|---|---|---|---|
| 5 | Pc 234 | chloride | Cl⁻ | 40 |
| 27 | Pc 251 | sodium bisulfate | ⁻O-S(=O)(=O)-ONa | 50 |
| 26 | Pc 250 | methanesulfonate | ⁻O-S(=O)(=O)-CH₃ | 56 |
| 18 | Pc 245 | sulfonate | ⁻O-S(=O)(=O)-(CH₂)₃-O-(CH₂CH₂O)~20-C₆H₄-C₈ | 87 |
| 14 | Pc 242 | sulforhodamine B ate | (sulforhodamine B structure) | 69 |
| 13 | Pc 241 | dimethylphosphinate | ⁻O-P(=O)(CH₃)₂ | 52 |
| 25 | Pc 249 | inosinate | (inosine monophosphate structure) | 39 |

|    | Pc     | name                                      | X⁻ | %  |
|----|--------|-------------------------------------------|----|----|
| 15 | Pc 243 | lactate                                   |    | 83 |
| 7  | Pc 235 | succinate                                 |    | 50 |
| 20 | Pc 246 | polyethylene glycol succinate             |    | 52 |
| 24 | Pc 248 | polyethylene glycol methyl ether succinate|    | 75 |
| 22 | Pc 247 | polyethylene glycol succinate             |    | 40 |
| 11 | Pc 239 | (+)-α-tocopherol succinate                |    | 80 |
| 6  | Pc 229 | malate                                    |    | 90 |
| 8  | Pc 236 | stearate                                  |    | 25 |
| 12 | Pc 240 | oleate                                    |    | 37 |
| 15 | Pc 243 | lactate                                   |    | 83 |
| 9  | Pc 237 | salicylate                                |    | 71 |
| 10 | Pc 238 | acetylsalicylate                          |    | 39 |
| 16 | Pc 244 | polydimethylsiloxane decanoate            |    | 93 |

FIG. 5 (cont.)

PHTHALOCYANINE SALT FORMULATIONS

FIELD OF INVENTION

The present invention is directed to pharmaceutical compositions including phthalocyanines or salts thereof suitable for use as photosensitizers for photodynamic therapy, and phthalocyanine compounds including attached free radical sources such as fatty acids.

BACKGROUND OF THE INVENTION

Photodynamic therapy, hereinafter also referred to as "PDT", is a process for treating cancer wherein visible light is used to activate a substance, such as a dye or drug, which then attacks the tumor tissue through one or more photochemical reactions, thereby producing a cell-killing, or cytotoxic, effect. It has been discovered that when certain photosensitizer compounds are applied to the human or animal body, they are selectively retained by cancerous tissue while being eliminated by healthy tissue. The tumor or cancerous tissue containing the photosensitizer can then be exposed to therapeutic light of an appropriate wavelength and at a specific intensity for activation. The light energy and the photosensitizer cause a photochemical reaction which kills the cells in which the photosensitizer resides.

Phthalocyanines, hereinafter also abbreviated as "Pcs", are a group of photosensitizer compounds having the phthalocyanine ring system. Phthalocyanines are azaporphyrins consisting of four benzoindole groups connected by nitrogen bridges in a 16-membered ring of alternating carbon and nitrogen atoms (i.e., $C_{32}H_{16}N_8$) which form stable chelates with metal and metalloid cations. In these compounds, the ring center is occupied by a metal ion (either a diamagnetic or a paramagnetic ion) that may, depending on the ion, carry one or two ligands. In addition, the ring periphery may be either unsubstituted or substituted. The synthesis and use of a wide variety of phthalocyanines in photodynamic therapy is described in International Publication WO 2005/099689. Phthalocyanines strongly absorb clinically useful red or near IR radiation with absorption peaks falling between about 600 and 810 nm, which potentially allows deep tissue penetration by the light.

Phthalocyanines are generally very stable to photofading caused by $^1O_2$. This is advantageous in many circumstances because, for example, special storage and handling techniques are not required. However, for PDT the photostability of a photosensitizer such as Pc 4 can also be disadvantageous. For example, the outer shell of a treated tumor could shield the inner core of the tumor from light and thus prevent the light necessary for the photodynamic therapy from reaching the inner core. It would therefore be advantageous in some situations to be able to formulate phthalocyanines in such a way as to decrease their stability without rendering them so unstable that they cannot function.

Phthalocyanines should be formulated to allow delivery in sufficient amounts to be therapeutically effective. Phthalocyanines such as Pc 4 have typically been formulated for systemic delivery in a solution of povidone, which is subsequently dissolved in a solution of Cremophor EL, ethanol, and saline (5:5:90 by volume), to provide phthalocyanine at a concentration of about 0.1 mg/mL for clinical use. For topical delivery, phthalocyanines have been formulated in a solution of povidone which is subsequently dissolved in a solution of Cremophor EL, ethanol, and propylene glycol (5:68:27 by volume), to again provide a concentration for clinical use of about 0.1 mg/mL. However, while these formulations are useable, they can be slow to provide effective concentrations of the phthalocyanine at the tumor site. In addition, the relative performance of various phthalocyanine salts in phthalocyanine formulations remains unknown.

Accordingly, there remains a need for the characterization of additional phthalocyanine salts and the development of additional formulations for their administration.

SUMMARY OF THE INVENTION

A series of OH-replaced phthalocyanine derivatives and salts were prepared and characterized with respect to, for example, their solubility in various solvents, their stability, and their ability to penetrate skin. Characterization of the phthalocyanine salts identified compounds appropriate for use in aqueous or oil-based pharmaceutically acceptable carriers, and various specific formulations such as creams, emulsions, or gels. The improved formulations provide better vehicles for systemic and topical administration of phthalocyanines for applications such as anticancer therapy. The improved formulations can, for example, provide better penetration or deliver phthalocyanines at higher concentration.

One aspect of the invention relates to pharmaceutical compositions including a pharmaceutically acceptable water-soluble salt of a phthalocyanine in an aqueous-based pharmaceutically acceptable carrier. The phthalocyanines include one or two axial ligands carrying amine functions forming a cation to which a polar anion associates. Examples of polar anions include malate, mesylate, inosate, dimethylphosphonate, methylsulfonate, and sulfonate anions. The pharmaceutical composition can also include a dispersant, and can provide either systemic or topical formulations, with examples of topical formulations including creams, gels, and films.

Another aspect of the invention relates to pharmaceutical compositions including a pharmaceutically acceptable oil-soluble salt of a phthalocyanine in an oil-based pharmaceutically acceptable carrier. The phthalocyanines include one or two axial ligands carrying amine functions forming a cation to which a non-polar anion associates. Examples of non-polar anions include α-tocopherol succinate and stearate anions. The pharmaceutical compositions can be formulated as a topical formulation such as an ointment.

A further aspect of the invention relates to phthalocyanine compounds including a free radical source. These compounds provide the advantage of tunable photostability as a result of the generation of free radicals which degrade the phthalocyanine compound. In one embodiment, the compound is a phthalocyanine polyunsaturated fatty acid salt, in which the phthalocyanine includes one or two axial ligands carrying amine functions forming a cation to which the polyunsaturatedfatty acid anion associates. Examples of polyunsaturated fatty acids are omega-3 fatty acids such as linolenic acid. In an alternate embodiment, the compound is a phthalocyanine polyunsaturated fatty acid ester in which one or two polyunsaturated fatty acids are attached through an ester ligand to the metal core of the phthalocyanine. Examples of polyunsaturated fatty acids may again include omega-3 fatty acids such as linolenic acid. In a further embodiment, the compound is a phthalocyanine compound including a substituted free radical source. The free radical source is attached to a phenyl ring along the outside edge of the phthalocyanine ring structure. The free radical source can be a polyunsaturated fatty acid, or it may be other polyunsatured compounds such as polyunsaturated alkenyl amides, polyunsaturated acyls, polyunsaturated alkenyl amines, or polyunsaturated alkenyl groups. The phthalocyanine compounds including free radical sources such as fatty acids can be used to provide pharmaceutical compositions by including them with a pharmaceutically acceptable carrier.

BRIEF DESCRIPTION OF THE DRAWINGS

The following is a brief description of the drawings which are presented for the purpose of illustrating the invention and not for the purpose of limiting them.

DETAILED DESCRIPTION OF THE INVENTION

Figure 1:
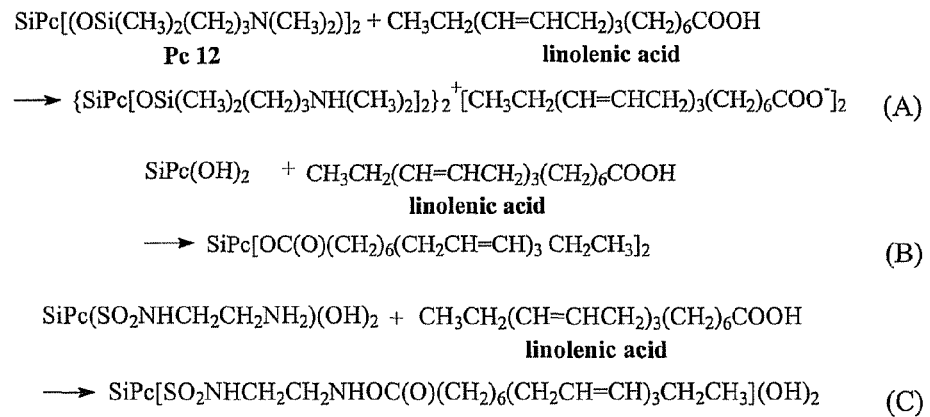
FIG. 1 is a set of chemical equations representing the attachment of linolenic acid to phthalocyanine compounds via (A) salt formation, (B) ester formation, or (C) substitution.

The present invention relates in part to pharmaceutical compositions including phthalocyanine compounds, particularly phthalycyanine salts, suitable for use in photodynamic therapy. These include hydroxy-replaced Si or Al phthalocyanines having a substituted amine axial ligand attached to the central metal, as well as phthalocyanines including two amine axial ligands or phthalocyanines bearing free radical sources such as fatty acids. The phthalocyanine compounds have various properties making them suitable for different applications such as systemic or topical formulations, or as tunable compounds with intermediate stability that allow for the activation of the photosensitizers at deep levels within tissue.

Definitions

The term "$C_{x-y}$acyl" refers to a group represented by the general formula:

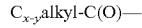

$C_{x-y}$alkyl-C(O)—

The term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively. When such alkenyl or alkynyl groups include more than one unsaturated bond, they can be referred to as polyunsaturated alkenyl or alkynyl groups.

The term "alkoxy" refers to an alkyl group having an oxygen attached thereto. Representative alkoxy groups include methoxy, ethoxy, propoxy, tert-butoxy and the like. An "ether" is two hydrocarbon groups covalently linked by an oxygen. Accordingly, the substituent of an alkyl that renders that alkyl an ether is or resembles an alkoxy.

The terms "amine" and "amino" are art-recognized and refer to both unsubstituted and substituted amines and salts thereof.

The term "aryl" as used herein includes 5-, 6-, and 7-membered substituted or unsubstituted single-ring aromatic groups in which each atom of the ring is carbon. Aryl groups include benzene, phenol, aniline, and the like.

The terms "carbocycle" and "carbocyclyl", as used herein, refer to a non-aromatic substituted or unsubstituted ring in which each atom of the ring is carbon.

The terms "heteroaryl" includes substituted or unsubstituted aromatic 5- to 7-membered ring structures, more preferably 5- to 6-membered rings, whose ring structures include one to four heteroatoms. Heteroaryl groups include, for example, pyrrole, furan, thiophene, imidazole, oxazole, thiazole, triazole, pyrazole, pyridine, pyrazine, pyridazine and pyrimidine, and the like.

The term "heteroatom" as used herein means an atom of any element other than carbon or hydrogen. Preferred heteroatoms are nitrogen, oxygen, phosphorus, and sulfur.

The terms "heterocyclyl" or "heterocyclic group" refer to substituted or unsubstituted non-aromatic 3- to 10-membered ring structures, more preferably 3- to 7-membered rings, whose ring structures include one to four heteroatoms.

The term "polyunsaturated fatty acid" refers to a fatty acid that contains more than one double bond. Fatty acids are carboxylic acids with an unbranched alkenyl group including at least four carbons. The multiple double bonds included in the alkenyl group can be either interrupted or conjugated. A polyunsaturated fatty acid attached by substitution may be referred to herein as a polyunsaturated $C_{4-24}$alkenyl ester.

The terms "PcIV" and "Pc 4", as used herein represent a compound having a structure of Formula (I), wherein M is $HOSiPcOSi(CH_3)_2(CH_2)_3N(CH_3)_2$.

The term "substituted" refers to moieties having substituents replacing a hydrogen on one or more carbons of the framework. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

Substituents on fused ring structures can be peripheral or non-peripheral substituents. A non-peripheral substituent, as defined herein, is a substituent which is adjacent (i.e., α) to the point of fusion between an outer phenyl ring and an inner pyrrole ring, as found in phthalocyanine compounds as exemplified by Formula (I) herein. A substituent is peripheral, on the other hand, when it is not a non-peripheral substitutent. For example, in Formula I provided herein, the substituents $R^2$, $R^3$, $R^6$, $R^7$, $R^{10}$, $R^{11}$, $R^{14}$, and $R^{15}$ are peripheral substituents.

A "therapeutically effective amount" of a compound with respect to the subject method of treatment, refers to an amount of the compound(s) in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

As used herein, the term "treating" or "treatment" includes reversing, reducing, or arresting the symptoms, clinical signs, and underlying pathology of a condition in manner to improve or stabilize a subject's condition.

With regard to the present invention, a series of phthalocyanine OH-replaced derivatives, phthalocyanine salts, and phthalocyanine OH-replaced drivative salts were prepared and evaluated for their suitability in phthalocyanine formulations. The various compounds were characterized by NMR and UV-vis spectroscopy, and in some cases by mass spectroscopy, which showed that the HOMO-LUMO separation of the phthalocyanine ring was not greatly affected by the exchange of other ligands of Pc 4 for the OH ligand or by the other modifications carried out. The physical state of the phthalocyanine salts was shown to be strongly influenced by the anion of the salt. Most of the phthalocyanine salts are solids at room temperature, but a few are liquids. Likewise, the solubility of the salts is strongly influenced by the anion, with some salts being soluble in polar solvents such as an aqueous solution and others being soluble in nonpolar solvents such as mineral oil.

Preparation and characterization of various phthalocyanine salts facilitated the development of other aspects of the invention, such as delivery systems for phthalocyanine salts. For example, oil-soluble phthalocyanine salts can be used in an ointment delivery system; and water-soluble phthalocyanine salts can be used to provide an intravenous delivery system; a gel delivery system; or a patch delivery system. Clearly, the phthalocyanine salts offer many avenues for creating useful delivery systems.

When properly formulated, phthalocyanine salt solutions can penetrate fairly quickly through polyurethane, cellulose, polyvinylidene fluoride and silicone membranes, pig keratomes, and human roof blisters, as evidenced by studies using Franz diffusion cells. Such work demonstrates that a number of phthalocyanine salt formulations are suitable for the topical delivery of phthalocyanines.

The salts chosen for this work can be selected from those formed by acids giving physiologically ubiquitous ions or intermediate metabolite ions in biochemical pathways, such as the acids designated as Class 1 by Stahl (Handbook of Pharmeceutical Salts; Stahl, P. H.; Wermuth, C. G. Eds; Wiley-CH: New York, 2002; p 9-18), or those formed by acids showing little toxicity and good tolerability.

In the compounds and compositions of the present invention, axial ligands carrying or terminating in an amine function can be attached to the central metal. It is believed that these complex axial ligands give the phthalocyanine compounds the ability to bind to the various species that assist in transporting the compositions to their targets, as well as enhance the ability of the phthalocyanines to bind to their specific target cells.

Phthalocyanine compounds of the invention generally have a structure of the following formula (I):

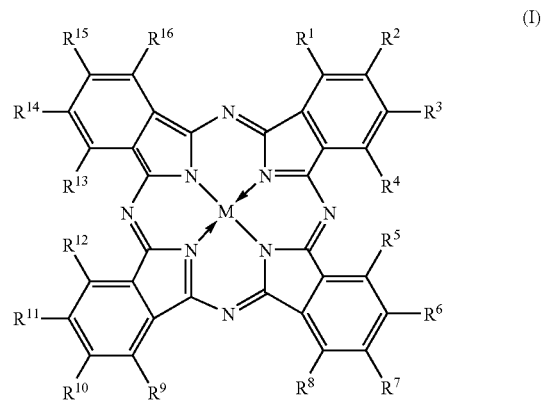

wherein M is $(R')_eX[OSi(CH_3)_2(CH_2)_aN^+(R'')_b(R''')_cY^-]_d$;
X is selected from Si or Al;
Y is a pharmaceutically acceptable salt-forming anion;
R' is selected from OH, $CH_3$, halogen, $OCH_3$, $OC(O)CH_3$, and $OC(O)CH_2CH_3$;
R'' is selected from H, $CH_3$, $C_2H_5$, $C_4H_9$, $C_4H_8NH$, $C_4H_8N$, $C_4H_8NCH_3$, $C_4H_8S$, $C_4H_8O$, $OC(O)CH_3$, $OC(O)$, CS, CO, OH, $C_4H_8N(CH_2)_3CH_3$, $(CH_2)_2N(CH_3)_2$, $(CH_2)_fN((CH_2)_g(CH_3))_2$, and an alkyl group having from 1 to 12 carbon atoms;
R''' is selected from H, $CH_3$, $SO_2CH_3$, $(CH_2)_2N(CH_3)_2$, $(CH_2)_{11}CH_3$, $C(S)NHC_6H_{11}O_5$, $(CH_2)_fN((CH_2)_g(CH_3))_2$, and an alkyl group having from 1 to 12 carbon atoms;
a is an integer from 2 to 4; b is an integer from 0 to 3; c is an integer from 0 to 2; d is 1 or 2; e is 0 or 1; f is an integer from 1 to 12; g is an integer from 1 to 11;
$R^1$, $R^4$, $R^5$, $R^8$, $R^9$, $R^{12}$, $R^{13}$, and $R^{16}$ are each independently selected from hydrogen, halogen, nitro, cyano, hydroxy, thiol, amino, and methyl; and
$R^2$, $R^3$, $R^6$, $R^7$, $R^{10}$, $R^{11}$, $R^{14}$, and $R^{15}$ are each independently selected from hydrogen, halogen, nitro, cyano, hydroxy, thiol, amino, carboxy, aryl, heteroaryl, carbocyclyl, heterocyclyl, $C_{1-6}$alkyl, $C_{1-6}$alkenyl, $C_{1-6}$alkynyl, $C_{1-6}$alkoxy, $C_{1-6}$acyl, $C_{1-6}$alkylcarbonyloxy, $C_{1-6}$carbocyclylalkyl, $C_{1-6}$aminoalkyl, $C_{1-6}$alkylamino, $C_{1-6}$thioalkyl, $C_{1-6}$alkylthio, $C_{1-6}$hydroxyalkyl, $C_{1-6}$alkyloxycarbonyl, $C_{1-6}$alkylaminocarbonyl, and $C_{1-6}$alkylcarbonylamino.

In some embodiments, d and e of formula (I) are both 1.
In certain embodiments, $R^1$-$R^{16}$ of the compound of formula (I) are independently selected from hydrogen, halogen, nitro, cyano, hydroxyl, thiol, amino, and methyl, while in other embodiments $R^1$-$R^{16}$ are all hydrogen.

In further embodiments, the group M is selected from the group consisting of $AlOSi(CH_3)_2(CH_2)_3N(CH_3)_2$; $CH_3SiOSi(CH_3)_2(CH_2)_3N(CH_3)_2$; $HOSiOSi(CH_3)_2(CH_2)_3N(CH_3)_2$; $HOSiOSi(CH_3)_2(CH_2)_4NHSO_2CH_3$; $HOSiOSi(CH_3)_2(CH_2)_3N(CH_2CH_3)(CH_2)_2N(CH_3)_2$; $HOSiOSi(CH_3)_2(CH_2)_3NC_4H_8O^-$; $HOSiOSi(CH_3)_2(CH_2)_4N(CH_3)_2$; $HOSiOSi(CH_3)_2(CH_2)_3NC_4H_8S$; $HOSiOSi(CH_3)_2(CH_2)_3N(CH_2)_3(CH_3)_2$; $HOSiOSi(CH_3)_2(CH_2)_3NCS$; $HOSiOSi(CH_3)_2(CH_2)_3N[(CH_2)_3N(CH_3)_2]_2$; $HOSiOSi(CH_3)_2(CH_2)_3NC_4H_8NCH_3$; $HOSiOSi(CH_3)_2(CH_2)_3NC_4H_8N(CH_2)_3CH_3$; $FSiOSi(CH_3)_2(CH_2)_3N(CH_3)_2$; $ClSiOSi(CH_3)_2$ $(CH_2)_3N(CH_3)_2$; $CH_3C(O)OSiOSi(CH_3)_2(CH_2)_3N(CH_3)_2$; $CH_3CH_2C(O)OSiOSi(CH_3)_2(CH_2)_3N(CH_3)_2$; and $CH_3OSiOSi(CH_3)_2(CH_2)_3N(CH_3)_2$.

In yet further embodiments, the group M is selected from the group consisting of $HOSiOSi(CH_3)_2(CH_2)_3N(CH_3)_2$; $FSiOSi(CH_3)_2(CH_2)_3N(CH_3)_2$; $ClSiOSi(CH_3)_2(CH_2)_3N(CH_3)_2$; $CH_3C(O)OSiOSi(CH_3)_2(CH_2)_3N(CH_3)_2$; $CH_3CH_2C(O)OSiOSi(CH_3)_2(CH_2)_3N(CH_3)_2$; and $CH_3OSiOSi(CH_3)_2(CH_2)_3N(CH_3)_2$, while in additional embodiments M is $HOSiOSi(CH_3)_2(CH_2)_3N(CH_3)_2$, which is designated Pc 4.

The salts used in the pharmaceutical compositions of the present invention are pharmaceutically acceptable salts; i.e., they are relatively non-toxic, inorganic and organic acid addition salts. These salts can be prepared in situ during the final isolation and purification of the photosensitizer(s), or by separately reacting a purified photosensitizer(s) in its free base form with a suitable organic or inorganic acid, and isolating the salt thus formed. In some embodiments, the salts include polar carboxylate anions, polar phosphonate anions, and polar sulfonate anions, which are used for pharmaceutical compositions including an aqueous-based carrier, while in other embodiments the salts include non-polar carboxylate anions, non-polar phosphonate anions, and non-polar sulfonate anions, which are used in oil-based carriers.

Improved phthalocyanine formulations can be obtained by identifying salts of phthalocyanines with characteristics that are especially suitable for the desired type of formulation. Many different phthalocyanine salts are available, and as described herein, the variation in the properties of phthalocyanine salts is quite large. For example, while the malate salt of Pc 4 (compound 6, Pc 229), the mesylate salt of Pc 4 (compound 26, Pc 250), the inosinate salt of Pc 4 (compound 25, Pc 249), the tocopherol salt of Pc 4 (compound 11, Pc 239), and many of the other salts of Pc 4 are solids at room temperature, as well as physiological temperatures, the sulfonate salt of Pc 4 (compound 18, Pc 245), and the siloxane salt of Pc 4 (compound 16, Pc 244) are liquids, as shown in Table 1. Liquid Pc 4 salts can be used in high-concentration formulations of Pc 4 for both systemic and topical use due to their availability in liquid form at room temperature.

TABLE 1

Physical State of Salts

| | | salt anion | | | mp |
|---|---|---|---|---|---|
| | | name | formula | state | (° C.) |
| 6 | Pc 229 | malate | (structure) | solid | 285 dec |
| 26 | Pc 250 | mesylate | (structure) | solid | 285 dec |
| 25 | Pc 249 | inosinate | (structure) | solid | 285 dec |
| 11 | Pc 239 | (+)-α-tocopherol succinate | (structure) | solid | 285 dec |
| 18 | Pc 245 | sulfonate | (structure) | liquid | |

TABLE 1-continued

Physical State of Salts

| | | salt anion | | | mp |
|---|---|---|---|---|---|
| | name | formula | | state | (° C.) |
| 16 Pc 244 | polydimethylsiloxane decanoate | 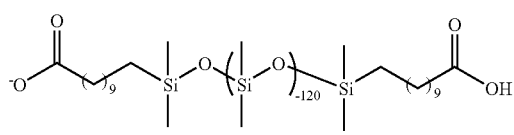 | | liquid | |

In some embodiments of the invention, the pharmaceutical composition includes pharmaceutically acceptable water-soluble phthalocyanine salts. Water-soluble phthalocyanine salts, as used herein, are phthalocyanine salts that show an appreciable and pharmaceutically useful solubility in water-based (i.e., aqueous) solutions. Water-soluble phthalocyanine salts include those with a solubility of about 20 mM or more, while in other embodiments they include those with a solubility of about 40 mM or more, in aqueous solution. Preferably, the aqueous solution also includes a dispersant such as Tween 80.

A number of phthalocyanine salts are water-soluble. Water soluble anions that can be present in phthalocyanine salts include polar carboxylate anions, polar phosphonate anions, and polar sulfonate anions. For example, the malate salt of Pc 4 (compound 6, Pc 229), the mesylate salt of Pc 4 (compound 26, Pc 250), and the inosinate salt of Pc 4 (compound 25, Pc 249), all show solubility in an aqueous solution, but little in hexanes or mineral oil (Nujol). The water solubility of a number of phthalocyanine salts such as the malate salt of Pc 4 (compound 6) provides compounds suitable for use in various water-based formulations, such as solution formulations for systemic use and of cream formulations (i.e., oil-in-water emulsion formulations) for topical use.

TABLE 2

Salt Concentration of Salts in Polar and Nonpolar Solvents

| | | salt anion | | salt concentration | | |
|---|---|---|---|---|---|---|
| | | | | 5.5 mM aqueous Tween 80 | hexanes | mineral oil |
| | | name | formula | (mM) | (mM) | (mM) |
| 6 | Pc 229 | malate | 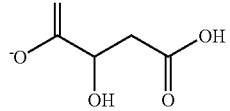 | 0.165 | 0.0006 | 0.0002 |
| 26 | Pc 250 | mesylate |  | 0.262 | 0.002 | 0.002 |
| 25 | Pc 249 | inosinate | 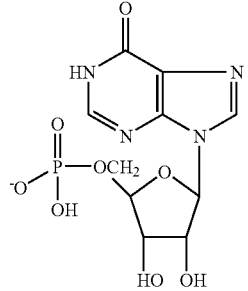 | 0.274 | 0.000 | 0.002 |
| 11 | Pc 239 | (+)-α-tocopherol succinate | 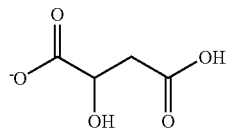 | 0.004 | 0.065 | 0.029 |

The identification of of water soluble phthalocyanine salts also makes possible the preparation of aqueous gel formulations of phthalocyanine salts. For example, a mixture of the malate salt of Pc 4 (compound 6), water, Tween 80 and hydroxyethylcellulose (HEC), as shown in Table 3, can provide a transparent blue gel. A mixture of the malate salt of Pc 4 (compound 6), water, Tween 80 and carbomer (Carbopol 934, Noveon, Cleveland, Ohio) can also provide a transparent blue gel. These phthalocyanine salt-containing gels provide gel formulations of phthalocyanine salts suitable for topical use. Thin films of the gels can also be dried to form coherent, stable, water-swellable films. These films provide formulations for phthalocyanine salt-containing patches that can be used for topical administration.

TABLE 3

Concentration of Salts in a Gel and a Film

| | | components | | | | product | |
|---|---|---|---|---|---|---|---|
| salt anion | | Pc 4 | $H_2O$ | Tween 80 | HEC | conc | |
| name | formula | (mg) | (mL) | (mg) | (mg) | type (mg/mL) | (%) |
| 6 Pc 229 | malate | 0.33 | 3.0 | 21.6 | | solution 0.11 | |
| | | 0.33 | 3.0 | 21.6 | 118 | gel | ~0.01 |
| | | 0.33 | | 21.6 | 118 | film | ~0.2 |

In some embodiments of the invention, the pharmaceutical composition includes pharmaceutically acceptable oil-soluble phthalocyanine salts. Oil-soluble phthalocyanine salts, as used herein, are phthalocyanine salts that show an appreciable and pharmaceutically useful solubility in relatively non-polar (e.g., oil) solutions. Examples of non-polar solutions include organic solvents such as dichloromethane, dimethylformamide, ethanol, toluene, and hexane, and oils such as mineral oil, vegetable oil, and petrolatum.

Oil soluble anions that can be present in phthalocyanine salts include non-polar carboxylate anions, non-polar phosphonate anions, and non-polar sulfonate anions. Examples of oil-soluble phthalocyanine salts include the tocopherol salt of Pc 4 (compound 11, Pc 239), which shows only slight solubility in aqueous solution, but significant solubility in hexanes and mineral oil, and even petrolatum (Vaseline), as shown in Table 2, and the stearate salt of Pc 4 (compound 8, Pc 236) The identification of the mineral oil and petrolatum solubility in some phthalocyanine salts facilitates the preparation of ointment formulations for topical use.

As already noted herein, the photostability of photodynamic therapy photosensitizers such as Pc 4 can be disadvantageous if, for example, they shield the inner core of a tumor from light. Accordingly, an additional embodiment of the invention provides phthalocyanine photosensitizers with tunable photostability. By "tunable" photostability, what is meant is that the photostability can be varied (i.e., "tuned") to a desired level by decreasing the photostability of a phthalocyanine photosensitizer by a desired amount. For example, the photostability can be decreased by an amount from about 10% to about 90%, (e.g., 20%, 30%, 40%, 50%, 60%, 70%, 80%, and intermediate amounts) relative to the photostability of an unmodified phthalocyanine.

One of the reasons for phthalocyanine's high photostability is that they are resistant to photofading caused by singlet oxygen ($^1O_2$). However, they are not resistant to photofading caused by free radicals. Accordingly, the photostability of phthalocyanines can be adjusted by placing a source of free radicals that can be activated by light or other means in their vicinity. Upon activation, the free radical source will release free radicals which will then degrade the phthalocyanine compound. A suitable source of free radicals, also referred to herein as a free radical source, is a compound including a polyunsaturated group (i.e., a polyunsaturated free radical source). However, free radicals can also be provided by other compounds that release free radicals upon exposure to light such as α-hydroxyfarnesylphosphonic acid, polyunsaturated $C_{4-24}$acyls, polyunsaturated $C_{4-24}$alkenyl amines, and polyunsaturated $C_{4-24}$alkenyls. Phthalocyanine compounds with tunable photostability can include one or more polyunsaturated free radical sources. For example, two polyunsaturated free radical sources can be attached to a phthalocyanine compound by attaching a polyunsaturated free radical source to each ligand bound to the central metal ion of the phthalocyanine compound, or multiple free radical sources can be substituted along the outside edge of the phthalocyanine ring.

A free radical source is placed in the vicinity of the phthalocyanine by attaching a polyunsaturated free radical source to the phthalocyanine. The polyunsaturated free radical source can be attached to the phthalocyanine in various different ways. For example, the polyunsaturated compound can be attached to the phthalocyanine through salt formation, ester formation, or substitution. Examples of attachment of the polyunsaturated compound linolenic acid to phthalocyanines are shown in FIG. 1. Salt formation typically occurs through association of an anion, such as that provided by a carboxyl group of a fatty acid, with a cationic amine group present in the phthalocyanine compound, such as one provided by an axial amine group. Ester formation, on the other hand, occurs at hydroxyl ligands such as those associated with the central metal in some phthalocyanine compounds. Substitution can occur in various ways, and is exemplified by an amine, ether, carbon linking atom which attaches the free radical source to a peripheral or non-peripheral position on the phthalocyanine ring.

As described above, not all of the phthalocyanines with tunable photostability are salts. For example, the phthalocyanine with tunable photostability can be a phthalocyanine polyunsaturated fatty acid ester, with a structure according to formula (I):

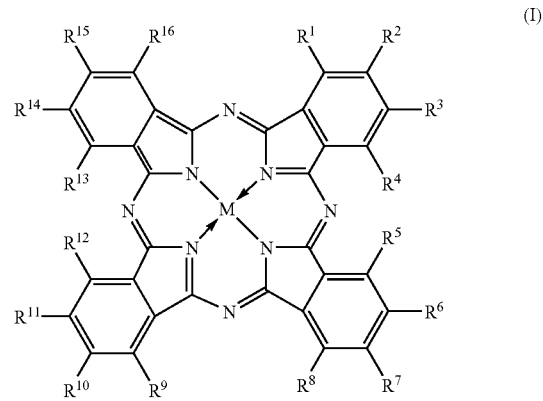

(I)

wherein M is $(R')_d X(R'')_e [OSi(CH_3)_2(CH_2)_a N(R''')_b (R'''')_c]_h$;

X is selected from Si or Al;

R' consists of a polyunsaturated fatty acid attached to X through an ester linkage;

R" is selected from OH, $CH_3$, halogen, $OCH_3$, $OC(O)CH_3$, and $OC(O)CH_2CH_3$ R'" is selected from H, $CH_3$, $C_2H_5$, $C_4H_9$, $C_4H_8NH$, $C_4H_8N$, $C_4H_8NCH_3$, $C_4H_8S$, $C_4H_8O$, $OC(O)CH_3$, $OC(O)$, CS, CO, OH, $C_4H_8N(CH_2)_3CH_3$, $(CH_2)_2N(CH_3)_2$, $(CH_2)_fN((CH_2)_g(CH_3))_2$, and an alkyl group having from 1 to 12 carbon atoms;

R"" is selected from H, $CH_3$, $SO_2CH_3$, $(CH_2)_2N(CH_3)_2$, $(CH_2)_{11}CH_3$, $C(S)NHC_6H_{11}O_5$, $(CH_2)_fN((CH_2)_g(CH_3))_2$, and an alkyl group having from 1 to 12 carbon atoms;

a is an integer from 2 to 4; b is an integer from 0 to 3; c is an integer from 0 to 2; d is 1 or 2; e is 0 or 1; f is an integer from 1 to 12; g is an integer from 1 to 11; h is [2−(d+e)])

$R^1$, $R^4$, $R^5$, $R^8$, $R^9$, $R^{12}$, $R^{13}$, and $R^{16}$ are each independently selected from hydrogen, halogen, nitro, cyano, hydroxy, thiol, amino, and methyl; and $R^2$, $R^3$, $R^6$, $R^7$, $R^{10}$, $R^{11}$, $R^{14}$, and $R^{15}$ are each independently selected from hydrogen, halogen, nitro, cyano, hydroxy, thiol, amino, carboxy, aryl, heteroaryl, carbocyclyl, heterocyclyl, $C_{1-6}$alkyl, $C_{1-6}$alkenyl, $C_{1-6}$alkynyl, $C_{1-6}$alkoxy, $C_{1-6}$acyl, $C_{1-6}$alkylcarbonyloxy, $C_{1-6}$carbocyclylalkyl, $C_{1-6}$aminoalkyl, $C_{1-6}$alkylamino, $C_{1-6}$thioalkyl, $C_{1-6}$alkylthio, $C_{1-6}$hydroxyalkyl, $C_{1-6}$alkyloxycarbonyl, $C_{1-6}$alkylaminocarbonyl, and $C_{1-6}$alkylcarbonylamino. Such phthalocyanine compounds can include one or two polyunsaturated free radical sources, such as an omega-3 fatty acid, attached to the central metal atom of the phthalocyanine compound.

Alternately, in other embodiments, the phthalocyanine with tunable photostability can be a phthalocyanine including a substituted polyunsaturated free radical source, with a structure according to formula (I):

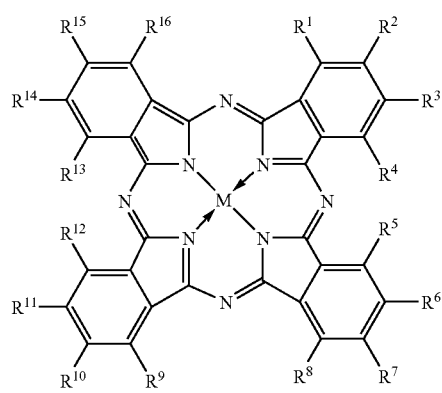

(I)

wherein M is $(R')_eX[OSi(CH_3)_2(CH_2)_aN(R'')_b(R''')_c]_d$;

X is selected from Si or Al;

R' is selected from OH, $CH_3$, halogen, $OCH_3$, $OC(O)CH_3$, and $OC(O)CH_2CH_3$;

R" is selected from H, $CH_3$, $C_2H_5$, $C_4H_9$, $C_4H_8NH$, $C_4H_8N$, $C_4H_8NCH_3$, $C_4H_8S$, $C_4H_8O$, $OC(O)CH_3$, $OC(O)$, CS, CO, OH, $C_4H_8N(CH_2)_3CH_3$, $(CH_2)_2N(CH_3)_2$, $(CH_2)_fN((CH_2)_g(CH_3))_2$, and an alkyl group having from 1 to 12 carbon atoms;

R'" is selected from H, $CH_3$, $SO_2CH_3$, $(CH_2)_2N(CH_3)_2$, $(CH_2)_{11}CH_3$, $C(S)NHC_6H_{11}O_5$, $(CH_2)_fN((CH_2)_g(CH_3))_2$, and an alkyl group having from 1 to 12 carbon atoms;

a is an integer from 2 to 4; b is an integer from 0 to 3; c is an integer from 0 to 2; d is an integer from 0 to 2; e is an integer from 0 to 2; f is an integer from 1 to 12; g is an integer from 1 to 11;

$R^1$, $R^4$, $R^5$, $R^8$, $R^9$, $R^{12}$, $R^{13}$, and $R^{16}$ are each independently selected from hydrogen, halogen, nitro, cyano, hydroxy, thiol, amino, and methyl; and $R^2$, $R^3$, $R^6$, $R^7$, $R^{10}$, $R^{11}$, $R^{14}$, and $R^{15}$ are each independently selected from hydrogen, halogen, nitro, cyano, hydroxy, thiol, amino, carboxy, aryl, heteroaryl, carbocyclyl, heterocyclyl, $C_{1-6}$alkyl, $C_{1-6}$alkenyl, $C_{1-6}$alkynyl, $C_{1-6}$alkoxy, $C_{1-6}$acyl, $C_{1-6}$alkylcarbonyloxy, $C_{1-6}$carbocyclylalkyl, $C_{1-6}$aminoalkyl, $C_{1-6}$alkylamino, $C_{1-6}$thioalkyl, $C_{1-6}$alkylthio, $C_{1-6}$hydroxyalkyl, $C_{1-6}$alkyloxycarbonyl, $C_{1-6}$alkylaminocarbonyl, $C_{1-6}$alkylcarbonylamino, and wherein at least one of $R^1$-$R^{16}$ is selected from the group of polyunsaturated free radical sources consisting of polyunsaturated $C_{4-24}$alkenyl esters, polyunsaturated $C_{4-24}$alkenyl amides, polyunsaturated $C_{4-24}$acyls, polyunsaturated $C_{4-24}$alkenyl amines, and polyunsaturated $C_{4-24}$alkenyls. Note that attachment of polyunsaturated free radical sources at the peripheral positions along the phthalocyanine ring can provide from 1 to 8 polyunsaturated free radical sources depending on how many of the peripheral positions are occupied by polyunsaturated free radical sources. In some embodiments, these polyunsaturated free radical sources can be omega-3 fatty acids.

A class of polyunsaturated free radical sources that can be attached to the phthalocyanine photosensitizers in some embodiments of the invention are polyunsaturated fatty acids. Polyunsaturated fatty acids are carboxylic acids with an unbranched alkenyl group with at least four carbons that include more than one double bond. Fatty acids can be short chain fatty acids with an unbranched alkenyl group of less than eight carbons, medium chain fatty acids with with an unbranched alkenyl group of eight to sixteen carbons, and long chain fatty acids with an unbranched alkenyl group of sixteen carbons or more. Examples of polyunsaturated fatty acids include linolenic acid, α-linolenic acid, arachidonic acid, eicosapentaenoic acid, and docosahexanoic acid (DHA). However, numerous other polyunsaturated fatty acids are known to those skilled in the art. See for example F. D. Gunstone, *Fatty Acid and Lipid Chemistry*; Blackie: London, UK, 1996, the disclosure of which is incorporated herein by reference.

Figure 2:
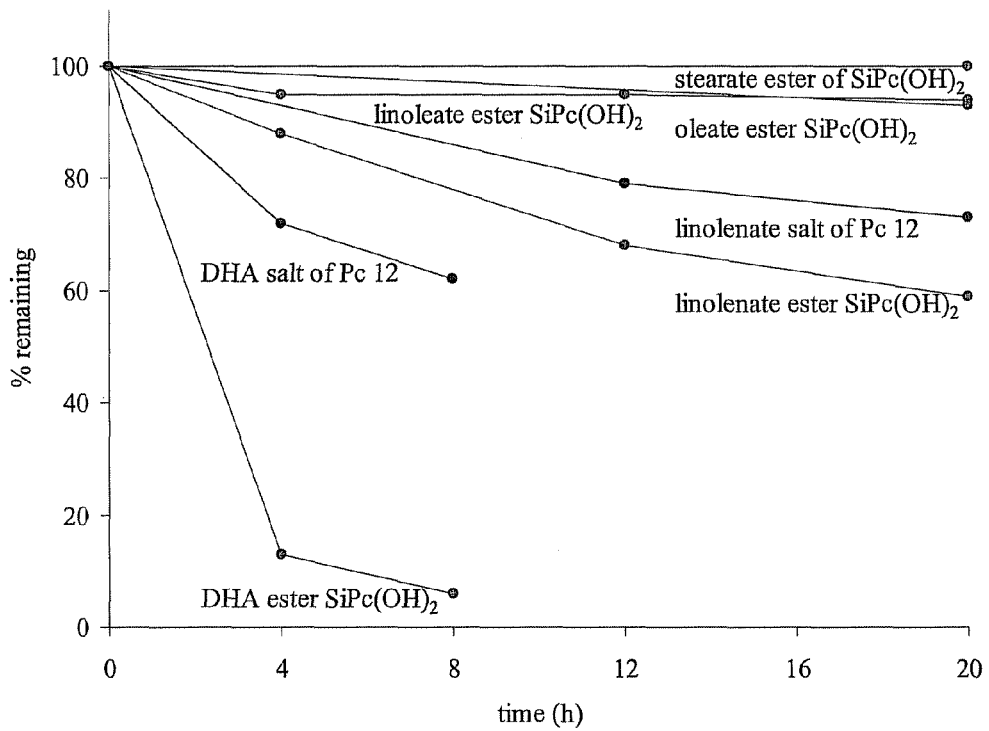
FIG. 2 is a graph illustrating the photofading of solutions of phthalocyanines with attached fatty acids upon exposure to visible light.

Omega fatty acids are fatty acids whose nomenclature is based on the location of the first double bond relative to the end of the unbranched alkenyl group. For example, embodiments of the invention can include omega-3 fatty acids, which are a group of fatty acids that include α-linolenic acid, eicosatrienoic acid, and docosahexanoic acid. As can be seen from the data provided in FIG. 2, which is discussed in further detail in the examples, increasing the amount of unsaturation in the fatty acids generally increases the ability of the fatty acids to act as a source of free radicals, which thereby decreases the stability of the phthalocyanine compound that they are attached to.

Methods for conducting photodynamic therapy are known in the art. See for example Thierry Patrice. *Photodynamic Therapy*; Royal Society of Chemistry, 2004. The pharmaceutical composition including phthalocyanines can be applied to an organ or tissue as a step in photodynamic therapy. In certain embodiments, the composition is applied to an epithelial, mesothelial, synovial, fascial, or serosal surface, including, but not limited to, the eye, esophagus, mucous membrane, bladder, joint, tendon, ligament, bursa, gastrointestinal, genitourinary, pleural, pericardial, pulmonary, or uroepithelial surfaces. In certain embodiments, the composition is applied to the surface of the skin.

Another aspect of the invention relates to a method for treating cancer comprising administering a pharmaceutical composition including a phthalocyanine or phthalocyanine salt to a surface of cancerous tissue and irradiating the surface. Cancer, as used herein, refers to a disease of abnormal and excessive cell proliferation, as known by those skilled in the art, and also includes precancerous conditions. The surface can be skin in the case of skin cancer, or an exposed internal surface in the case of other types of cancer. Skin cancers include, but are not limited to basal cell carcinoma, squamous cell carcinoma, and melanoma.

Pharmaceutical compositions including phthalocyanines or phthalocyanine salts can also be used to treat various other diseases or disorders. For example, pharmaceutical compositions of phthalocyanine salts can be used to purge bone marrow for autologous bone marrow transplantation, purge viruses from whole blood or blood components, treat psoriasis, treat warts, treat macular degeneration, or treat intraarterial plaques.

The present invention provides various phthalocyanine or phthalocyanine salt compositions that can be used to prepare formulations for systemic or topical administration. Systemic administration includes delivery of an aqueous solution, preferably a buffered aqueous solution, including a phthalocyanine salt. Systemic formulations typically also include a dispersant. Systemic administration is typically done parenterally (e.g., intravenously or intramuscularly). However, systemic administration can also be carried out by oral administration.

Topical administration of phthalocyanines or phthalocyanine salts can be accomplished using various different formulations such as powders, sprays, ointments, pastes, creams, lotions, gels, solutions, or patches. The active component may be mixed under sterile conditions with a pharmaceutically acceptable carrier, and with any preservatives, buffers, or propellants which may be required. The ointments, pastes, creams, solutions, foams, lacquers, oils and gels may contain excipients in addition to phthalocyanine(s). These formulations may contain a phthalocyanine salt within or on micro or nanoparticles, liposomes, beads, polymer matrices, sponges, osmotic pumps, or other structures.

Phthalocyanines or phthalocyanine salts can be formulated as ointments or creams for topical administration. Ointments are homogeneous, semi-solid preparations intended for external application to the skin or mucous membranes. They are used as emollients or for the application of active ingredients to the skin for protective, therapeutic, or prophylactic purposes and where a degree of occlusion is desired. Ointments can be formulated using hydrophobic, hydrophilic, or water-emulsifying bases to provide preparations for various applications. Creams, on the other hand, are semi-solid emulsions; i.e., a mixture of oil and water. They are divided into two types: oil-in-water creams which are composed of small droplets of oil dispersed in a continuous aqueous phase, and water-in-oil creams which are composed of small droplets of water dispersed in a continuous oily phase.

Phthalocyanines and phthalocyanine salts can also be administered by aerosol. This is accomplished by preparing an aqueous aerosol, liposomal preparation, or solid particles containing the compound. A nonaqueous (e.g., fluorocarbon propellant) suspension could be used. Sonic nebulizers are preferred because they minimize exposing the agent to shear, which can result in degradation of the compound. Ordinarily, an aqueous aerosol is made by formulating an aqueous solution or suspension of the agent together with conventional pharmaceutically acceptable carriers and stabilizers.

As described herein, phthalocyanines and phthalocyanine salts can also be formulated for delivery as a gel. Gel formulations comprising a phthalocyanine salt may be prepared according to U.S. Pat. Nos. 6,617,356 or 5,914,334, the disclosures of which are incorporated herein in their entirety. In addition, phthalocyanine-containing gels can be dried to form films suitable for phthalocyanine administration.

Transdermal patches have the added advantage of providing controlled delivery of a phthalocyanine to the body. Such dosage forms can be made by dissolving or dispersing the agent in the proper medium. Absorption enhancers can also be used to increase the flux of the photosensitizer(s) into the skin. The rate of such flux can be controlled by either providing a rate controlling membrane or dispersing the agent in a polymer matrix or gel.

Phthalocyanine formulations can also be delivered transdermally using microneedles. See for example Arora et al., International Journal of Pharmaceutics, 364, pg. 227-236 (2008), which describes micro-scale devices for transdermal drug delivery.

Delivery of phthalocyanines across an epithelial, epidermal, serosal or mucosal surface may be accomplished using application of an electrical current and a charged solvent solution, such as iontophoresis.

"Pharmaceutically acceptable carrier" as used herein means a pharmaceutically acceptable material, composition or vehicle, such as a liquid or solid filler, diluent, excipient, solvent or encapsulating material, involved in carrying or transporting the subject chemical from one organ or portion of the body, to another organ or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose, and sucrose; starches, such as corn starch and potato starch; cellulose, and its derivatives, such as sodium carboxymethyl cellulose, ethyl cellulose, and cellulose acetate; powdered tragacanth; malt; gelatin; talc; excipients, such as cocoa butter and suppository waxes; oils, such as peanut oil, cottonseed oil, safflower oil, sesame oil, olive oil, corn oil, and soybean oil; glycols, such as propylene glycol; polyols, such as glycerin, sorbitol, mannitol, and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

In some embodiments of the invention, aqueous-based or oil-based pharmaceutically acceptable carriers can be used. An aqueous-based pharmaceutically acceptable carrier is a polar solution primarily consisting of water, and including solutions such as pyrogen-free water, isotonic saline, Ringer's solution, and phosphate buffer solutions. Oil-based pharmaceutically acceptable carriers, on the other hand, are relatively non-polar solutions consisting primarily of oils or other relatively non-polar organic solvents. Examples of oil-based pharmaceutically acceptable carriers include various organic solvents, mineral oil, vegetable oil, and petrolatum.

The specific process utilized to synthesize the phthalocyanine salts and phthalocyanines with attached free radical sources of the present invention, and the enhanced results produced through the use of these new compounds for photodynamic therapy, are more particularly described below in the following examples.

EXAMPLES

General Synthetic Pathway for OH-Replaced Derivatives and Salts.

Pc 4 was prepared by the method of Li et al. as described in U.S. Pat. No. 5,763,602. The $SiPcCl_2$ used was primarily purchased from an organometallics supplier (Gelest, Tullytown, Pa.). The organosilicon reagents were purchased from the same supplier. The other reagents and solvents were purchased from chemical vendors (e.g., Aldrich, Milwaukee, Wis.; Fisher Scientific, Pittsburgh, Pa.; and Acros Organics, Morris Plains, N.J.). Most of the chemicals were of reagent grade. Compounds which are temperature sensitive, such as inosinic acid, were stored in a refrigerator. Pyruvic acid was purified and dried by partial distillation. The preparation of numerous other phthalocyanine derivatives is described in international patent publication WO 2005/099689, the disclosure of which is incorporated by reference herein.

Figure 3:
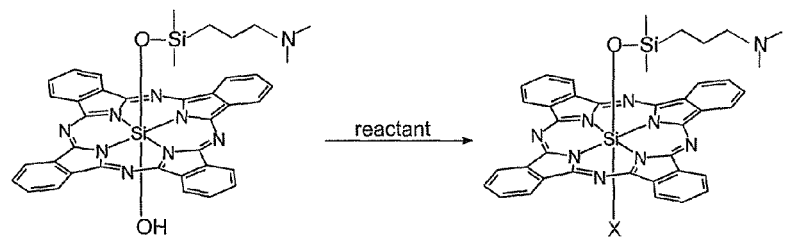
FIG. 3 is a reaction scheme showing the synthesis of hydroxy-replaced derivatives of Pc 4.
Figure 4:
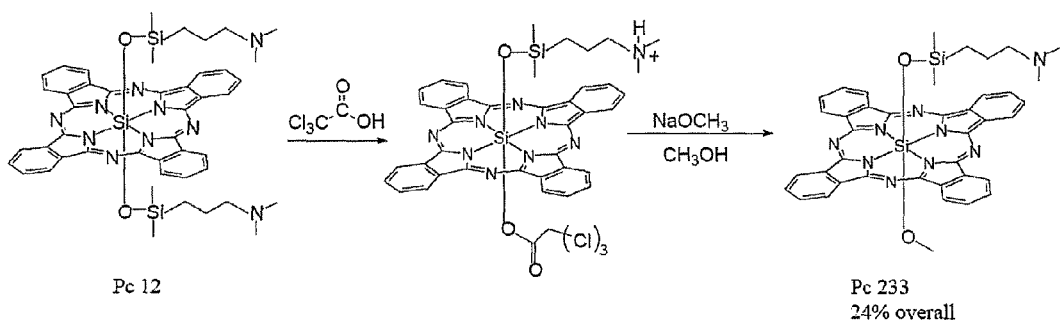
FIG. 4 is a reaction scheme showing the synthesis of the methoxy hydroxy-replaced derivative of Pc 4.

Silicon OH-replaced derivatives fluoro compound 1, acetoxy compound 2, and propionoxy compound 3 were prepared from Pc 4 by straightforward ligand exchange reactions, as shown in FIG. 3. The use of boron trifluoride etherate to carry out a reaction such as the synthesis of fluoro compound 1 is provided by Cheng et al., J. Phys. Chem. A, 107, pg. 3503-3514 (2003). Methoxy compound 4 was prepared by a two-step procedure from Pc 12, as shown in FIG. 4.

Figure 5:
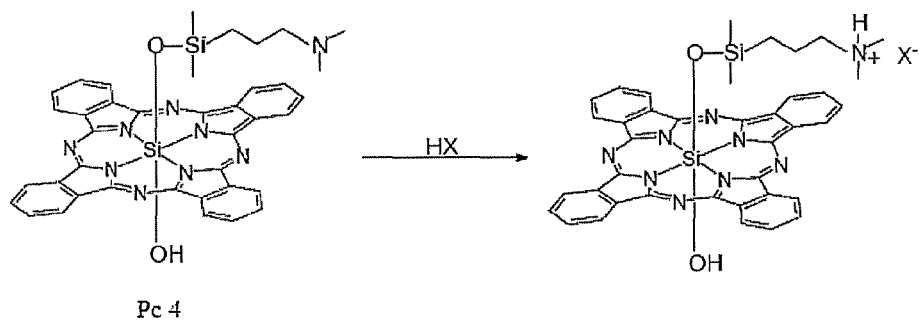
FIG. 5 is a reaction scheme showing the synthesis and structure of various Pc 4 salts.

Salts. The salts were prepared by straightforward acid-base reactions, as shown in FIG. 5. This synthetic approach was possible because Pc 4 is a moderate base with an estimated $pK_b$ of 4.3. In fact, at pH 7.4 (physiological pH) Pc 4 exists as a salt. In blood, for example, it probably exists mostly as Pc 4-HCl since blood has a relatively high concentration of $Cl^-$.

Figure 6:
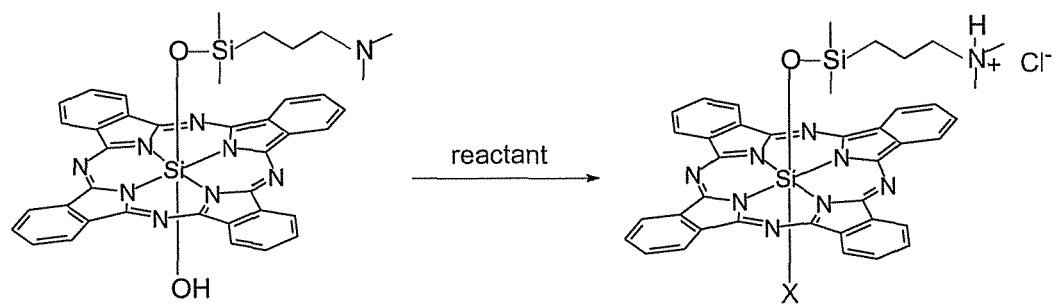
FIG. 6 is a reaction scheme showing the synthesis of hydroxy-replaced derivatives of Pc 4 in their salt form.

OH-Replaced Derivative Salts. The OH-replaced derivative salts were prepared as shown in FIG. 6. The use of thionyl chloride in the preparation of the chloro-chloride compound 28, is advantageous because both $SOCl_2$ and the reaction byproducts are volatile. For the preparation of pyruvoxychloride compound 29, pyruvyl chloride proved to be a convenient reactant.

Figure 7:
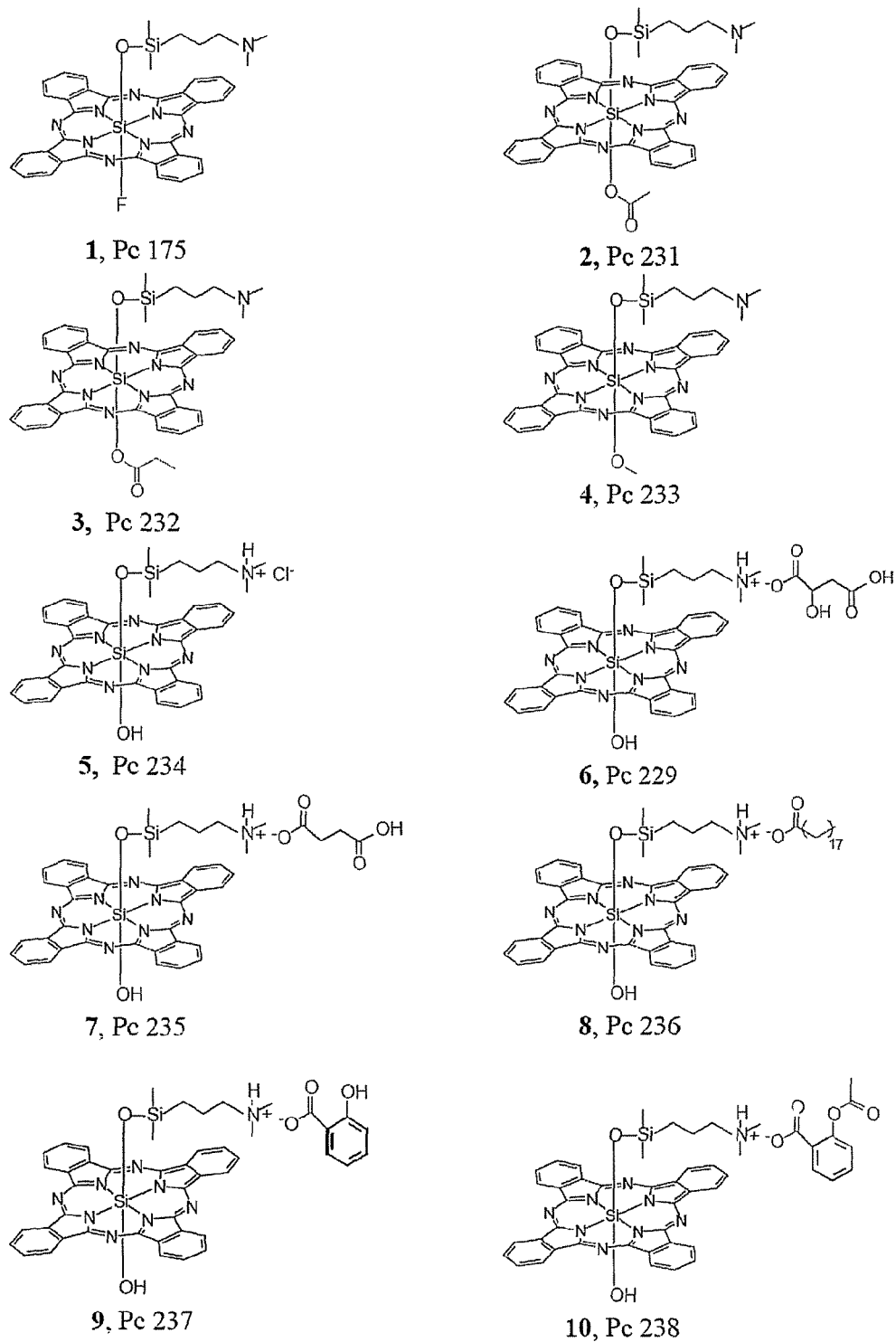
FIG. 7 is a list showing the structure of a number of phthalocyanine salt compounds of the present invention.
Figure 7:
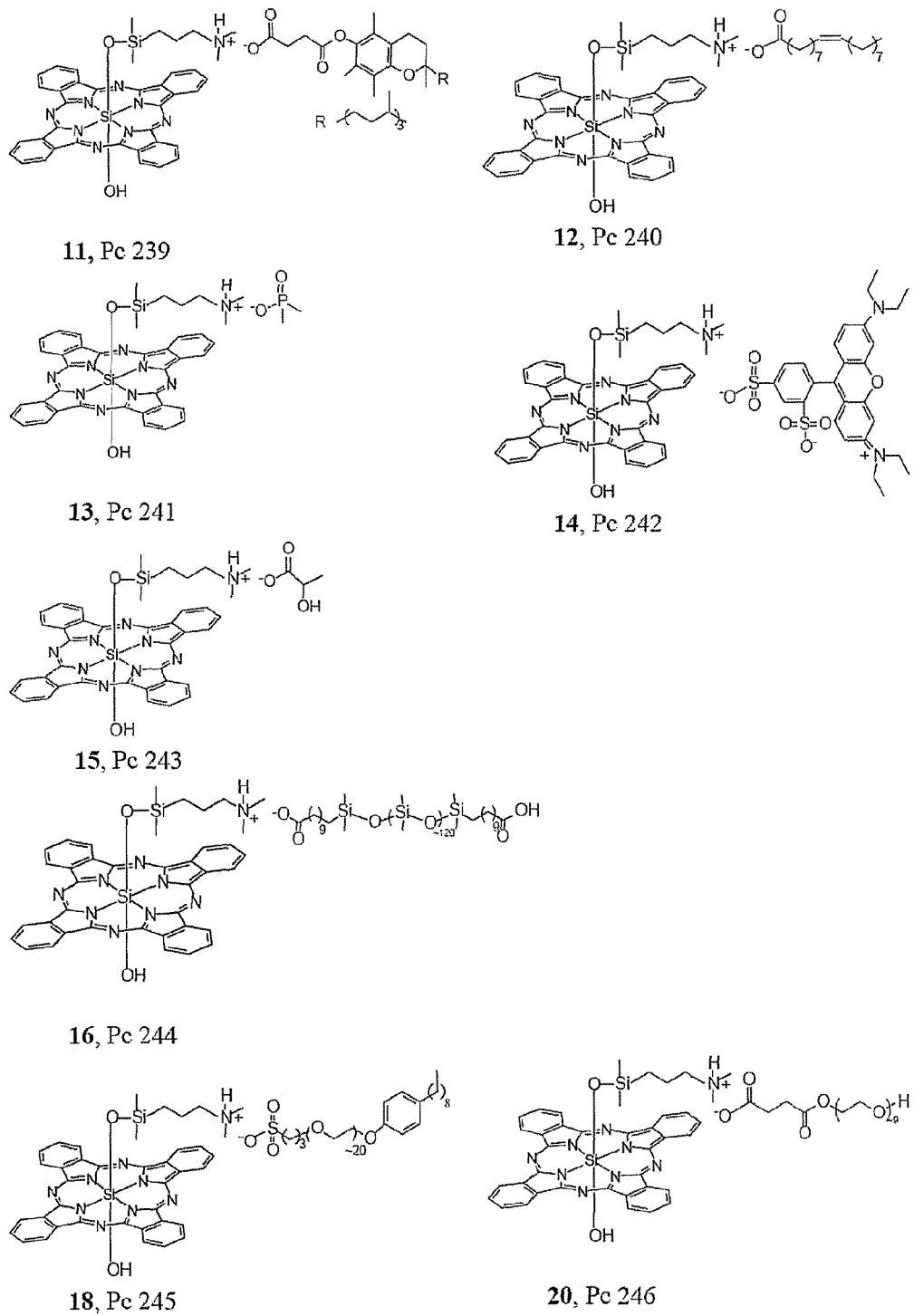
Figure 7:
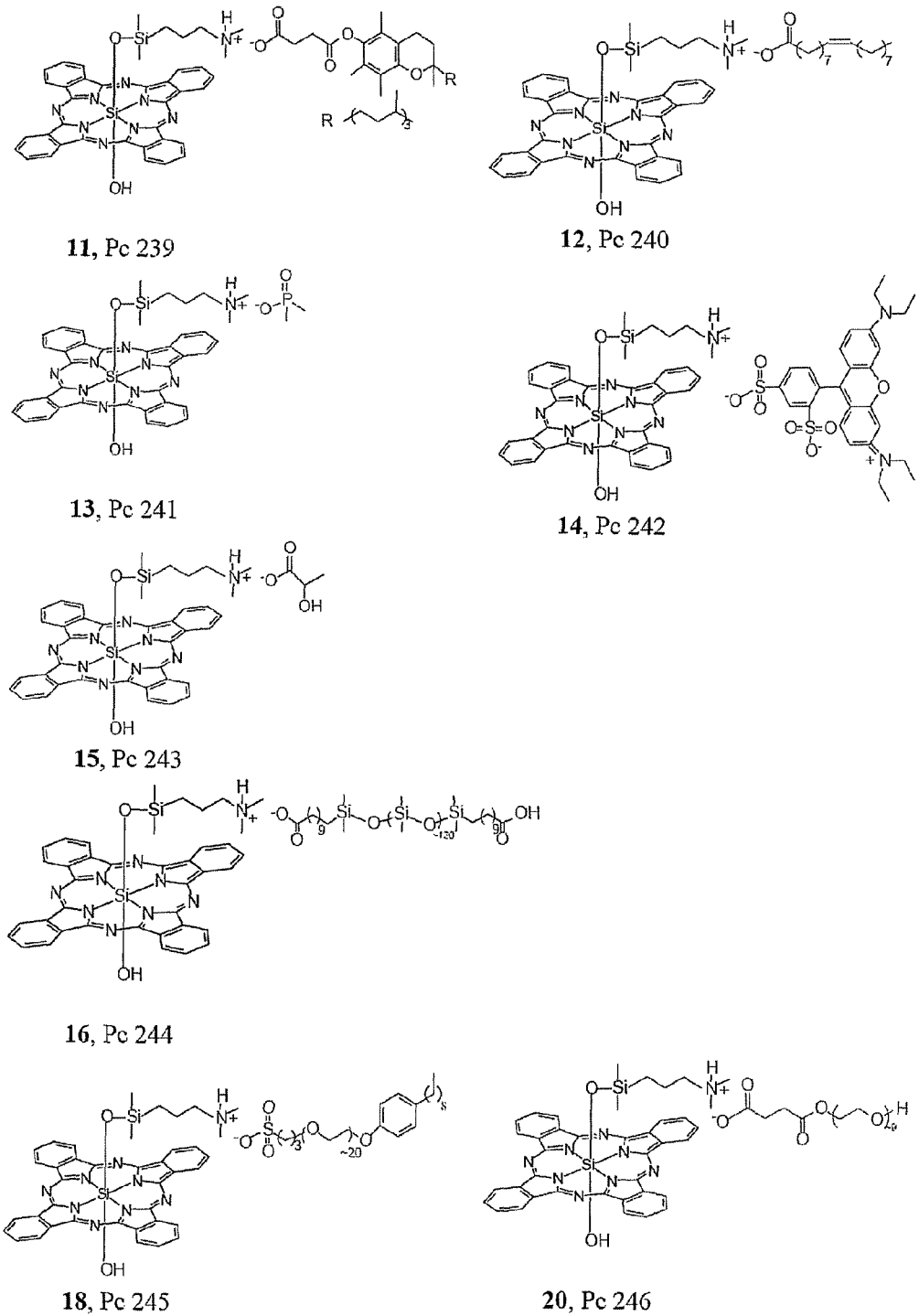
Figure 7:
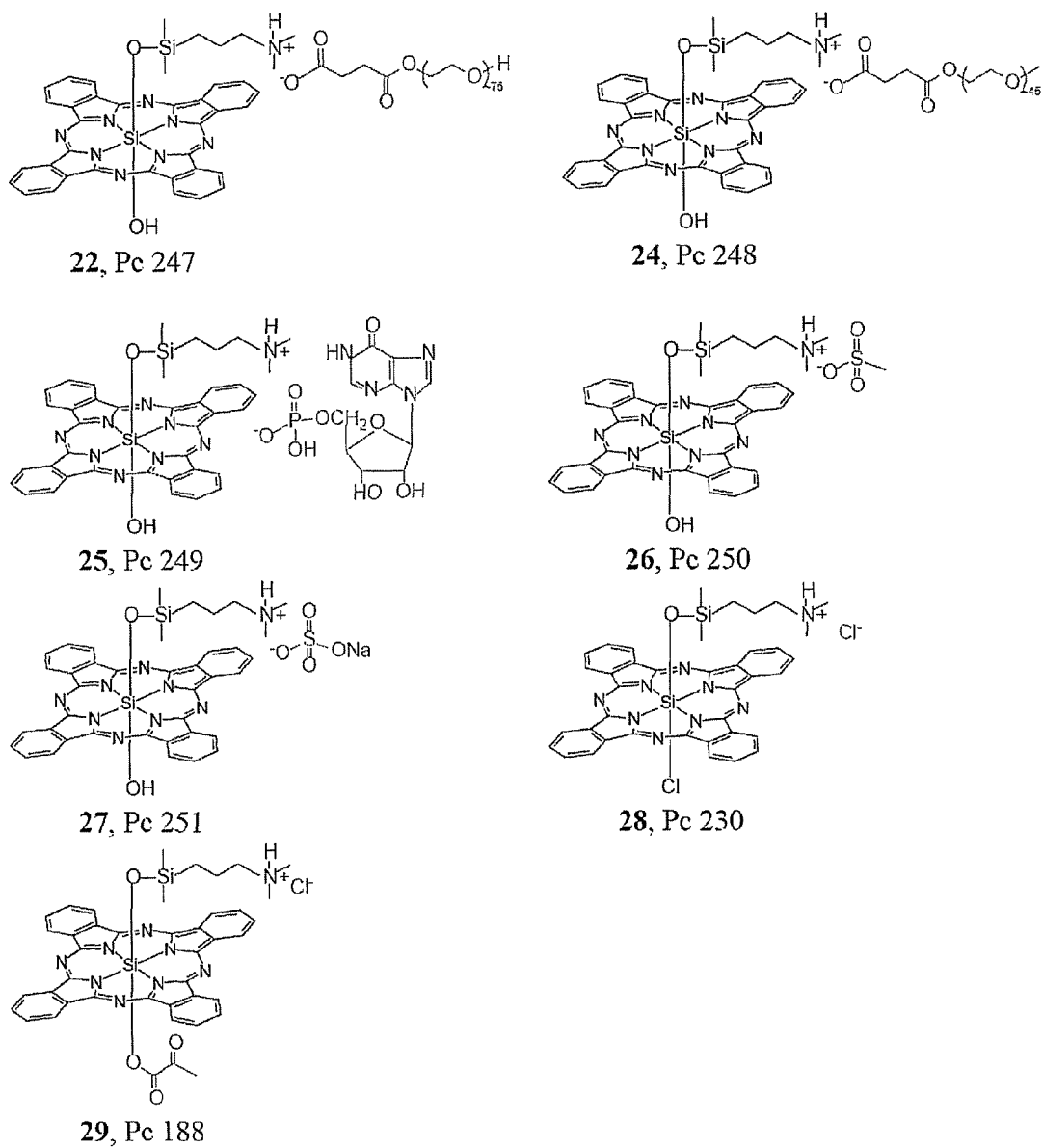

A list showing the structures of the phthalocyanine photosensitizer compounds prepared in the examples below is provided in FIG. 7.

Example 1

Syntheses of OH-Replaced Derivatives of Pc 4

$FSiPcOSi(CH_3)_2(CH_2)_3N(CH_3)_2$, PC 175, Compound 1. Under Ar, boron trifluoride diethyl etherate (0.4 mL, 3 mmol) was added dropwise to a suspension of $HOSiPcOSi(CH_3)_2$ $(CH_2)_3N(CH_2)_2$, Pc 4, (25 mg, 0.035 mmol) in toluene (15 mL). The product was stirred for 30 minutes, treated sequentially with pyridine (10 mL) and water (15 mL), and separated. The organic layer was evaporated to dryness by rotary evaporation (room temperature), and the solid was chromatographed (basic $Al_2O_3V$, $CH_3CH_2OH$), washed ($CH_3CN$), air dried, and weighed (14 mg, 0.019 mmol, 55%). UV-vis $(CH_2Cl_2)$ $\lambda_{max}$, mn (log $\epsilon$): 674 (5.4). NMR ($CDCl_3$): $\delta$ 9.66 (m, 8H, 1, 4-Pc H), 8.35 (m, 8H, 2, 3-Pc H), 1.57 (s, 6H, $NCH_3$), 0.83 (t, 2H, $SiCH_2CH_2CH_2$), $-1.06$ (m, 2H, $SiCH_2CH_2$), $-2.20$ (t, 2H, $SiCH_2$), $-2.81$ (s, 6H, $SiCH_3$). HRMS-ESI (m/z): $[M+H]^+$ calcd for M as $C_{39}H_{34}N_9FOSi_2$, 720.2487; found, 720.2477.

Compound 1 is a blue solid. It is soluble in $CH_2Cl_2$, dimethylformamide and ethanol, moderately soluble in toluene, and insoluble in hexanes. Compound 1 is stable in air.

$CH_3C(O)OSiPcOSi(CH_3)_2(CH_2)_3N(CH_3)_2$, Pc 231, Compound 2. Under Ar, a mixture of Pc 4 (17 mg, 0.024 mmol), acetic anhydride (0.10 mL, 1.0 mmol) and xylene (20 mL) was partly distilled (5 mL distillate); refluxed for 1 hour, filtered, and evaporated to dryness by rotary evaporation (room temperature). The solid was chromatographed (basic $Al_2O_3V$, $CH_2Cl_2$), washed ($CH_3CN$), air dried, and weighed (9 mg, 0.012 mmol, 50%). UV-vis $(CH_2Cl_2)$ $\lambda_{max}$, nm (log $\epsilon$): 672 (5.4). NMR ($CDCl_3$): $\delta$ 9.66 (m, 8H, 1, 4-Pc H), 8.35 (m, 8H, 2, 3-Pc H), 1.58 (s, 6H, $NCH_3$), 0.82 (t, 2H, $SiCH_2CH_2CH_2$), $-0.97$ (s, 3H, $OCOCH_3$), $-1.10$ (m, 2H, $SiCH_2CH_2$), $-2.22$ (t, 2H, $SiCH_2$), $-2.82$ (s, 6H, $SiCH_3$). HRMS-ESI (m/z): $[M+H]^+$ calcd for M as $C_{41}H_{37}N_9O_3Si_2$, 760.2636; found, 760.2617: $[M+H]^+$ calcd for M as $^{12}C_{40}{}^{13}CH_{37}N_9O_3Si_2$, 761.2660; found, 761.2653.

Compound 2 is a blue solid. It is soluble in $CH_2Cl_2$, dimethylformamide and ethanol, moderately soluble in toluene, and insoluble in hexanes. Compound 2 is stable in air.

$CH_3CH_2C(O)OSiPcOSi(CH_3)_2(CH_2)_3N(CH_3)_2$, Pc 232, Compound 3. Under Ar, a mixture of $HOSiPcOSi(CH_3)_2$ $(CH_2)_3N(CH_2)_2$, Pc 4 (42 mg, 0.058 mmol), propionic anhydride (0.25 mL, 1.9 mmol) and xylene (22 mL; dried by distillation, 3 mL distillate) was distilled slowly for 2 h (5 mL distillate), filtered, and evaporated to dryness by rotary evaporation (room temperature). The [0001] solid was chromatographed (basic $Al_2O_3V$, $CH_2Cl_2$), washed ($CH_3CN$), air dried, and weighed (14 mg, 0.018 mmol, 31%). UV-vis $(CH_2Cl_2)$ $\lambda_{max}$, mn (log $\epsilon$): 672 (5.4). NMR ($CDCl_3$): $\delta$ 9.66 (m, 8H, 1, 4-Pc H), 8.35 (m, 8H, 2, 3-Pc H), 1.61 (s, 6H, $NCH_3$), 0.88 (t, 2H, $SiCH_2CH_2CH_2$), $-0.78$ (m, 2H, $OCOCH_2$), $-1.05$ (m, 2H, $SiCH_2CH_2$), $-1.28$ (m, 3H, $OCOCH_2CH_3$), $-2.22$ (t, 2H, $SiCH_2$), $-2.80$ (s, 6H, $SiCH_3$). HRMS-ESI (m/z): [M+H]+ calcd for M as $C_{42}H_{39}N_9O3Si_2$, 774.2793; found, 774.2796: [M+H]+ calcd for M as 12C4113CH39N9O3Si2, 775.2817; found, 775.2816.

Compound 3 is a blue solid. It is soluble in $C_{H2}C_{l2}$, dimethylformamide and ethanol, moderately soluble in toluene, and insoluble in hexanes. Compound 3 is stable in air.

$CH_3OSiPcOSi(CH_3)_2(CH_2)_3N(CH_3)_2$, Pc 233, Compound 4. A solution of $SiPc[OSi(CH_3)_2(CH_2)_3N(CH_2)_2]_2$, Pc 12, (60 mg, 0.068 mmol), trichloroacetic acid (60 mg, 0.37 mmol) and $CH_2Cl_2$ (50 mL) was stirred for 5 h, treated sequentially with pyridine (10 mL) and water (15 mL), and separated. The organic layer was evaporated to dryness by rotary evaporation (room temperature), and the solid was treated with a solution of $NaOCH_3$ (4.8 mg, 0.089 mmol) and $CH_3OH$ (50 mL). The mixture was stirred for 2 h and evaporated to dryness by rotary evaporation (room temperature), and the solid was chromatographed (basic Al2O3 III, $CH_2Cl_2$), washed ($CH_3CN$), air dried, and weighed (12 mg, 0.016 mmol, 24%). UV-vis($CH_2Cl_2$) $\lambda_{max}$, nm (log $\epsilon$): 674 (5.4). NMR ($CDCl_3$): $\delta$ 9.64 (m, 8H, 1, 4-Pc H), 8.33 (m, 8H, 2, 3-Pc H), 1.57 (s, 6H, $NCH_3$), 0.83 (t, 2H, $SiCH_2CH_2CH_2$), $-1.11$ (m, 2H, $SiCH_2CH_2$), $-1.82$ (s, 3H, $OCH_3$), $-2.27$ (t, 2H, $SiCH_2$), $-2.87$ (s, 6H, $SiCH_3$). HRMS-FAB (m/z): [M+H]+ calcd for $C_{40}H_{37}N_9O_2Si_2$, 732.2687; found, 732.2690.

Compound 4 is a blue solid. It is soluble in $CH_2Cl_2$, dimethylformamide and ethanol, moderately soluble in toluene, and insoluble in hexanes. Compound 4 is stable in air.

Example 2

Syntheses of Pc 4 Salts $[HOSiPcOSi(CH_3)_2(CH_2)_3NH(CH_3)_2]^+Cl^-$, Pc 234, Compound 5. A mixture of $HOSiPcOSi(CH_3)_2(CH_2)_3N(CH_2)_2$, Pc 4, (7.5 mg, 0.010 mmol), SOCl$_2$ (0.6 mg, 0.005 mmol) and toluene (3 mL) was stirred for 10 min at −78° C., diluted with ether (3 mL), and filtered. The solid was air dried, chromatographed (Biobeads, Hercules, Calif.; S-X3, toluene), washed (CH$_3$CN), air dried, and weighed (3 mg, 0.004 mmol, 40%). UV-vis (DMF) $\lambda_{max}$, nm (log ϵ): 669 (5.4). NMR (CDCl$_3$): δ 9.35 (m, 8H, 1, 4-Pc H), 8.29 (m, 8H, 2, 3-Pc H), 1.93 (d, 6H, NCH3), 1.21 (t, 2H, SiCH$_2$CH$_2$CH$_2$), −1.05 (m, 2H, SiCH$_2$CH$_2$), −2.28 (t, 2H, SiCH$_2$), −2.94 (s, 6H, SiCH$_3$).

Pc 234 is blue solid. It is soluble in CH$_2$Cl$_2$, dimethylformamide and moderately soluble in toluene, and insoluble in hexanes.

[HOSiPcOSi(CH$_3$)$_2$(CH$_2$)$_3$NH(CH$_2$)$_{21}$]$^+$[OC(O)CHOHCH$_2$C(O)OH]$^-$, Pc 229, Compound 6. A solution of Pc 4 (10 mg, 0.014 mmol), L-(−)-malic acid (2.3 mg, 0.017 mmol) and ethanol (20 mL) was stirred for 30 min and dried by rotary evaporation (room temperature). The solid was chromatographed (Biobeads, S-X3, toluene), washed (CH$_3$CN), air dried, and weighed (10.7 mg, 0.013 mol, 90%). UV-vis (toluene) $\lambda_{max}$, nm (log ϵ): 670 (5.0). NMR (CDCl$_3$): δ 9.38 (m, 8H, 1, 4-Pc H), 8.30 (m, 8H, 2, 3-Pc H), 3.96 (d, H, HOC(O)CH$_2$CH), 2.53 (m, 2H, HOC(O)CH$_2$), 1.95 (s, 6H, NCH$_3$), 1.25 (t, 2H, SiCH$_2$CH$_2$CH$_2$), −1.17 (m, 2H, SiCH$_2$CH$_2$), −2.27 (t, 2H, SiCH$_2$), −2.94 (s, 6H, SiCH$_3$). HRMS-MALDI (m/z): [M-OH—C(O)OCHOHCH$_2$C(O)OH]$^+$ calcd for M as C$_{43}$H$_{41}$N$_9$O7Si$_2$, 700.2425; found, 700.2452, 700.2421.

Pc 229 is blue solid. It is soluble in CH$_2$Cl$_2$, dimethylformamide and ethanol, moderately soluble in toluene, and insoluble in hexanes.

[HOSiPcOSi(CH$_3$)$_2$(CH$_2$)$_3$NH(CH$_3$)$_2$]$^+$[OC(O)(CH$_2$)$_2$C(O)OH]$^-$, Pc 235, Compound 7. A solution of Pc 4 (7 mg, 0.010 mmol), succinic acid (2.3 mg, 0.019 mmol) and CH$_2$Cl$_2$ (10 mL) was stirred for 30 min and evaporated to dryness by rotary evaporation (room temperature). The solid was chromatographed (Biobeads, S-X3, toluene), washed (CH$_3$CN), air dried, and weighed (4 mg, 0.005 mmol, 50%). UV-vis (CH$_2$Cl$_2$) $\lambda_{max}$, nm (log ϵ): 672 (5.4). NMR (CDCl$_3$): δ 9.35 (m, 8H, 1, 4-Pc H), 8.29 (m, 8H, 2, 3-Pc H), 2.30 (s, 2H, OC(O)CH2), 2.30 (s, 2H, HOC(O)CH$_2$CH$_2$), 1.89 (s, 6H, NCH$_3$), 1.18 (t, 2H, SiCH$_2$CH$_2$CH$_2$), −1.18 (m, 2H, SiCH$_2$CH$_2$), −2.29 (t, 2H, SiCH$_2$), −2.95 (s, 6H, SiCH$_3$).

Pc 235 is blue solid. It is soluble in CH$_2$Cl2, dimethylformamide and ethanol, moderately soluble in toluene, and insoluble in hexanes.

[HOSiPcOSi(CH$_3$)$_2$(CH$_2$)$_3$NH(CH$_3$)$_2$]$^+$[OC(O)(CH$_2$)$_{16}$CH$_3$]$^-$, Pc 236, Compound 8. A solution of Pc 4 (3 mg, 0.004 mmol), stearic acid (8.9 mg, 0.031 mmol) and CH$_2$Cl$_2$ (5 mL) was stirred for 2 h and evaporated to dryness by rotary evaporation (room temperature). The solid was chromatographed (Biobeads, S-X3, toluene), washed (CH$_3$CN), air dried, and weighed (1 mg, 0.001 mmol, 25%). UV-vis (CH$_2$Cl$_2$) $\lambda_{max}$, nm (log ϵ): 672 (5.4). NMR (CDCl$_3$): δ 9.46 (m, 8H, 1, 4-Pc H), 8.30 (m, 8H, 2, 3-Pc H), 2.26 (t, H, OC(O)CH$_2$), 1.87 (s, 6H, NCH$_3$), 1.44 (m, 2H, OC(O)CH$_2$CH$_2$), 1.24 (t, 2H, SiCH$_2$CH$_2$CH$_2$), 1.15 (m, 28H, OC(O)CH2CH$_2$(CH$_2$)$_{14}$), 0.86 (t, 3H, OC(O)CH$_2$CH$_2$(CH$_2$)$_{14}$CH$_3$), −1.11 (m, 2H, SiCH$_2$CH$_2$), −2.26 (t, 2H, SiCH$_2$), −2.91 (s, 6H, SiCH$_3$).

Pc 236 is blue solid. It is soluble in CH$_2$Cl$_2$, dimethylformamide and ethanol, moderately soluble in toluene, and slightly soluble in hexanes.

[HOSiPcOSi(CH$_3$)$_2$(CH$_2$)$_3$NH(CH$_3$)$_2$]$^+$[2-(HO)C$_6$H$_4$C(O)O]$^-$, Pc 237, Compound 9. A solution of Pc 4 (5.2 mg, 0.007 mmol), salicylic acid (3.8 mg, 0.028 mmol) and CH$_2$Cl$_2$ (5 mL) was stirred for 30 min and evaporated to dryness by rotary evaporation (room temperature). The solid was chromatographed (Biobeads, S-X3, CH$_2$Cl$_2$), washed (CH$_3$CN), air dried, and weighed (4.7 mg, 0.005 mmol, 71%). UV-vis (CH$_2$Cl$_2$) $\lambda_{max}$, nm (log ϵ): 672 (5.4). NMR (CDCl$_3$): δ 9.35 (m, 8H, 1, 4-Pc H), 8.28 (m, 8H, 2, 3-Pc H), 7.58 (d, 1H, 6-C$_6$H$_4$C(O)O), 7.20 (t, 1H, 4-C$_6$H$_4$C(O)O), 6.79 (d, 1H, 3-C$_6$H$_4$C(O)O), 6.67 (d, 1H, 5-C$_6$H$_4$C(O)O), 2.00 (s, 6H, NCH$_3$), 1.31 (t, 2H, SiCH$_2$CH$_2$CH$_2$), −1.13 (m, 2H, SiCH$_2$CH$_2$), −2.26 (t, 2H, SiCH$_2$), −2.95 (s, 6H, SiCH$_3$). HRMS-FAB (m/z): [M+H-2-(OH)C$_6$H$_4$C(O)O]$^+$ calcd for M as C$_{46}$H$_{41}$N$_9$O$_5$Si$_2$, 718.2531; found, 718.2529.

pppc 237 is blue solid. It is soluble in CH$_2$Cl$_2$, dimethylformamide and ethanol, moderately soluble in toluene, and insoluble in hexanes.

[HOSiPcOSi(CH$_3$)$_2$(CH$_2$)$_3$NH(CH$_2$)$_2$]$^+$[2-(CH$_3$OC(O))C$_6$H$_4$C(O)O]$^-$, Pc 238, Compound 10.

A solution of Pc 4 (16.6 mg, 0.023mmol), acetylsalicylic acid (aspirin, 6.3 mg, 0.035 mmol) and CH$_2$Cl$_2$ (5 mL) was stirred for 20 min and evaporated to dryness by rotary evaporation (room temperature). The solid was chromatographed (Biobeads, Hercules, Calif.; S-X3, toluene), washed (CH$_3$CN), air dried, and weighed (8.1 mg, 0.009 mmol, 39%). UV-vis (CH$_2$Cl$_2$) $\lambda_{max}$, nm (log ϵ): 672 (5.4). NMR (CDCl$_3$): δ 9.38 (m, 8H, 1, 4-Pc H), 8.29 (m, 8H, 2, 3-Pc H), 7.60 (d, 1H, 6-C$_6$H$_4$C(O)O), 7.21 (t, 1H, 4-C$_6$H$_4$C(O)O), 6.79 (d, 1H, 3-C$_6$H$_4$C(O)O), 6.65 (d, 1H, 5-C$_6$H$_4$C(O)O), 1.95 (s, 3H, 2-(CH$_3$C(O)O)C$_6$H$_4$C(O)O),1.93 (s, 6H, NCH$_3$), 1.26 (t, 2H, SiCH$_2$CH$_2$CH$_2$), −1.21 (m, 2H, SiCH$_2$CH$_2$), −2.29 (t, 2H, SiCH$_2$), −2.94 (s, 6H, SiCH$_3$). HRMS-FAB (m/z): [M+H-2-(CH$_3$OC(O))C$_6$H$_4$C(O)O]$^+$ calcd for M as C$_{48}$H$_{43}$N$_9$O$_6$Si$_2$, 718.2531; found, 718.2522.

Pc 238 is blue solid. It is soluble in CH$_2$Cl2, dimethylformamide and ethanol, moderately soluble in toluene, and insoluble in hexanes.

[HOSiPcOSi(CH$_3$)$_2$(CH$_2$)$_3$NH(CH$_2$)$_2$]$^+$[C$_{33}$H$_{53}$O$_5$]$^-$, Pc 239, Compound 11. A solution of Pc 4 (7.7 mg, 0.011 mmol), (+)-α-tocopherol succinate (C$_{33}$H$_{54}$O$_5$, 11.2 mg, 0.022 mmol) and CH$_2$Cl$_2$ (3 mL) was stirred for 20 min and evaporated to dryness by rotary evaporation (room temperature). The solid was chromatographed (Biobeads, S-X3, CH$_2$Cl$_2$), washed (CH$_3$CN, Et$_2$O), air dried, and weighed (10 mg, 0.009 mmol, 80%). UV-vis (CH$_2$Cl$_2$) $\lambda_{max}$, nm (log ϵ): 672 (5.4). NMR (CDCl$_3$): δ 9.38 (m, 8H, 1, 4-Pc H), 8.30 (m, 8H, 2, 3-Pc H), 2.70 (t, 2H, bp-4 H), 2.58 (t, 2H, HOC(O)CH$_2$CH$_2$), 2.58 (m, 2H, HOC(O)CH$_2$), 2.06 (s, 3H, bp-7 CH$_3$), 1.97 (s, 3H, bp-7 CH$_3$), 1.93 (s, 3H, bp-5 CH$_3$), 1.93 (s, 6H, NCH$_3$), 1.6-1.8 (m, 2H, bp-3 H), 1.4-1.6 (m, 2H, bp-2 H), 1.22 (s, 3 H, bp-2 CH$_3$), 1.15 (t, 2H, SiCH$_2$CH$_2$CH$_2$), 1.0-1.3 (m, 19H, bp-R CH$_2$), 0.84 (m, 12H, bp-R CHCH$_3$), −1.19 (m, 2H, SiCH$_2$CH$_2$), −2.29 (t, 2H, SiCH$_2$), −2.93 (s, 6H, SiCH$_3$).

Pc 239 is blue solid. It is soluble in CH$_2$Cl$_2$, dimethylformamide and ethanol, moderately soluble in toluene, and slightly soluble in hexanes.

[HOSiPcOSi(CH$_3$)$_2$(CH$_2$)$_3$NH(CH$_2$)$_2$]$^+$[CH$_3$(CH$_2$)$_7$CH=CH(CH$_2$)$_7$C(O)O]$^-$, Pc 240, Compound 12. A solution of Pc 4 (7.9 mg, 0.011 mmol), oleic acid (11.2 mg, 0.040 mmol) and CH$_2$Cl$_2$ (10 mL) was stirred for 2 h and evaporated to dryness by rotary evaporation (room temperature). The solid was chromatographed (Biobeads, S-X3, CH$_2$Cl$_2$), washed (CH$_3$CN), air dried, and weighed (4.1 mg, 0.004 mmol, 37%). UV-vis (CH$_2$Cl$_2$) $\lambda_{max}$, nm (log ϵ): 672 (5.4). NMR (CDCl$_3$): δ 9.35 (m, 8H, 1, 4-Pc H), 8.27 (m, 8H, 2, 3-Pc H), 5.31 (m, 2H, OC(O)(CH$_2$)$_7$CH=CH), 2.11 (t, H, OC(O)CH$_2$), 2.00 (m, 4H, OC(O)(CH$_2$)$_6$CH$_2$CH=CHCH$_2$), 1.67 (s, 6H, NCH$_3$), 1.47 (m, 2H, OC(O)CH$_2$CH$_2$), 1.24 (m, 20H, OC(O)CH$_2$CH$_2$(CH$_2$)$_4$CH$_2$CH=CHCH$_2$(CH$_2$)$_6$), 1.00 (t, 2H, SiCH$_2$CH$_2$CH$_2$), 0.87 (m, 3H, OC(O)CH$_2$CH$_2$ (CH$_2$)$_4$CH$_2$CH=CHCH$_2$(CH$_2$)$_6$CH$_3$), −1.21 (m, 2H, SiCH$_2$CH$_2$), −2.36 (t, 2H, SiCH$_2$), −2.98 (s, 6H, SiCH$_3$).

Pc 240 is blue solid. It is soluble in CH$_2$Cl$_2$, dimethylformamide and ethanol, moderately soluble in toluene, and insoluble in hexanes.

[HOSiPcOSi(CH$_3$)$_2$(CH$_2$)$_3$NH(CH$_2$)$_2$]$^+$[(CH$_3$)$_2$P(O)O]$^-$, Pc 241, Compound 13. A mixture of Pc 4 (15 mg, 0.021 mmol), dimethylphosphinic acid (3 mg, 0.032 mmol) and toluene (2 mL) was stirred for 30 min and evaporated to dryness by rotary evaporation (room temperature). The solid was chromatographed (Biobeads, Hercules, Calif.; S-X3, toluene), washed (CH$_3$CN), air dried, and weighed (8.8 mg, 0.011 mmol, 52%). UV-vis (CH$_2$Cl$_2$) $\lambda_{max}$, nm (log $\epsilon$): 672 (5.4). NMR (CDCl$_3$): δ 9.38 (m, 8H, 1, 4-Pc H), 8.29 (m, 8H, 2, 3-Pc H), 1.89 (s, 6H, NCH$_3$), 1.21 (t, 2H, SiCH$_2$CH$_2$CH$_2$), 1.12 (s, 3H, CH$_3$P(O)O), 1.09 (s, 3H, CH$_3$P(O)O), −1.15 (m, 2H, SiCH$_2$CH$_2$), −2.29 (t, 2H, SiCH$_2$), −2.95 (s, 6H, SiCH$_3$).

Pc 241 is blue solid. It is soluble in CH$_2$Cl$_2$, dimethylformamide and ethanol, moderately soluble in toluene, and insoluble in hexanes.

[HOSiPcOSi(CH$_3$)$_2$(CH$_2$)$_3$NH(CH$_2$)$_2$]$^+$[C$_{27}$H$_{29}$N$_2$O$_7$S$_2$]$^-$, Pc 242, Compound 14. A solution of Pc 4 (12 mg, 0.017 mmol), sulforhodamine B (10 mg, 0.017 mmol) and CH$_2$Cl$_2$ (5 mL) was stirred for 1 h and evaporated to dryness by rotary evaporation (room temperature). The solid was chromatographed (Biobeads, S-X3, CH$_2$Cl$_2$), washed (toluene), air dried, and weighed (15 mg, 0.012 mmol, 69%). UV-vis (CH$_2$Cl$_2$) $\lambda_{max}$, nm (log $\epsilon$): 669 (5.5). NMR (CDCl$_3$): δ 9.39 (m, 8H, 1, 4-Pc H), 8.30 (m, 8H, 2, 3-Pc H), 8.39 (s, 1H, h-H), 7.94 (d, 1H, g-H), 7.20 (d, 1H, f-H), 6.96 (d, 2H, e-H), 6.68 (d, 2H, d-H), 6.58 (s, 2H, c-H), 3.49 (m, 4H, b-H), 2.18 (s, 6H, NCH$_3$), 1.35 (t, 2H, SiCH$_2$CH$_2$CH$_2$), 1.23 (t, 6H, a-H), −1.06 (m, 2H, SiCH$_2$CH$_2$), −2.23 (t, 2H, SiCH$_2$), −2.94 (s, 6H, SiCH$_3$). HRMS-FAB (m/z): [M+H—C$_{27}$H$_{29}$N$_2$O$_7$S$_2$]$^+$ calcd for M as C$_{66}$H$_{66}$N$_{11}$O$_9$S$_2$Si$_2$, 718.2531; found, 718.2512.

Pc 242 is purple solid. It is soluble in CH$_2$Cl$_2$, dimethylformamide and ethanol, moderately soluble in toluene, and insoluble in hexanes.

[HOSiPcOSi(CH$_3$)$_2$(CH$_2$)$_3$NH(CH$_3$)$_2$]$^+$[CH$_3$CHOHC(O)O]$^-$, Pc 243, Compound 15. A solution of Pc 4 (8.4 mg, 0.012 mmol), a solution of L-lactic acid in CH$_2$Cl$_2$ (47 mM, 0.50 mL, 0.024 mmol) and CH$_2$Cl$_2$ (10 mL) was stirred for 30 min and evaporated to dryness by rotary evaporation (room temperature). The solid was chromatographed (Biobeads, S-X3, CH$_2$Cl$_2$), washed (toluene), air dried (room temperature), and weighed (8.0 mg, 0.010 mmol, 83%). UV-vis (CH$_2$Cl$_2$) $\lambda_{max}$, nm (log $\epsilon$): 672 (5.4). NMR (CDCl$_3$): δ 9.37 (m, 8H, 1, 4-Pc H), 8.28 (m, 8H, 2, 3-Pc H), 3.78 (t, H, C(O)OCHOH), 1.76 (s, 6H, NCH$_3$), 1.11 (d, 3H, C(O)OCHOHCH$_3$), 1.08 (t, 2H, SiCH$_2$CH$_2$CH$_2$), −1.18 (m, 2H, SiCH$_2$CH$_2$), −2.32 (t, 2H, SiCH$_2$), −2.96 (s, 6H, SiCH$_3$).

Compound 15 is blue solid. It is soluble in CH$_2$Cl$_2$, dimethylformamide and ethanol, moderately soluble in toluene, and insoluble in hexanes.

[HOSiPcOSi(CH$_3$)$_2$(CH$_2$)$_3$NH(CH$_3$)$_2$]$^+$[(HOC(O)(CH$_2$)$_{10}$Si(CH$_3$)$_2$)(Si(CH$_3$)$_2$O)$_{\sim 120}$(Si(CH$_3$)$_2$(CH$_2$)$_{10}$C(O)O]$^-$, Pc 244, Compound 16. A solution of Pc 4 (10 mg, 0.014 mmol), (HOC(O)(CH$_2$)$_{10}$Si(CH$_3$)$_2$)(Si(CH$_3$)$_2$O)$_{\sim 120}$(Si(CH$_3$)$_2$(CH$_2$)$_{10}$C(O)OH (mol wt~10,000, 172 mg, ~0.0172 mmol, Gelest,) and CH$_2$Cl$_2$(10 mL) was stirred for 2 h and evaporated to dryness by rotary evaporation (50° C.). The solid was vacuum dried (room temperature), and weighed (170 mg, ~0.0159 mmol, 93%). UV-vis (CH$_2$Cl$_2$), nm (log $\epsilon$): 672 (5.4). NMR (CDCl$_3$): δ 9.38 (m, 8H, 1, 4-Pc H), 8.28 (m, 8H, 2, 3-Pc H), 3.66 (d, H, OC(O)CH$_2$), 2.29 (m, 2H, OC(O)CH$_2$CH$_2$), 1.67 (s, 6H, NCH$_3$), 1.25 (m, 20 H, OC(O)(CH$_2$)$_{10}$), 1.00 (t, 2H, Si(CH$_3$)$_2$CH$_2$CH$_2$CH$_2$), 0.06 (m, ~720 H, (OSi(CH$_3$)$_2$)$_{\sim 120}$(CH$_3$)$_2$Si(CH$_2$)$_{10}$C(O)O), −1.20 (m, 2H, SiCH$_2$CH$_2$), −2.35 (t, 2H, SiCH$_2$), −2.97 (s, 6H, SiCH$_3$).

Compound 16 is viscous blue oil. It is soluble in CH$_2$Cl$_2$, dimethylformamide and ethanol, moderately soluble in toluene, and insoluble in hexanes. Compound 16 decomposed to Pc 4 and the carboxysiloxane when it was chromatographed (Biobeads S-X3, CH$_2$Cl$_2$).

4-C$_9$H$_{19}$C$_6$H$_4$-1-(OCH$_2$CH$_2$)$_{\sim 20}$O(CH$_2$)$_3$SO$_3$H, Compound 17. A solution of 4-C$_9$H$_{19}$C$_6$H$_4$1-1-(OCH$_2$CH$_2$)$_{\sim 20}$O(CH$_2$)$_3$SO$_3$K (mol wt~1262, 1.06 g, ~0.84 mmol, Aldrich) and H$_2$O (30 mL) was passed down a Dowex 50WX8-200 ion-exchange resin (Aldrich) column (1.5×20 cm), and concentrated by rotary evaporation to an oil (room temperature) (11 mL, ~0.076 mM, 9.64%). NMR (CDCl$_3$): 7.20 (m, 2H, 2,6-C$_6$H$_4$ H), 6.82 (m, 2H, 3,5-C$_6$H$_4$H), 3.95 (d, 2H, SO$_3$CH$_2$), 3.60 (m, 80H, C$_9$H$_{19}$C$_6$H$_4$(OCH$_2$CH$_2$)$_{\sim 20}$O(CH$_2$)$_3$SO$_3$), 2.62 (m, 2H, SO$_3$CH$_2$CH$_2$), 1.24 (m, 19H, C$_9$H$_{19}$C$_6$H$_4$(OCH$_2$CH$_2$)$_{\sim 20}$O(CH$_2$)$_3$SO$_3$).

Compound 17 is colorless oil. It is soluble in CH$_2$Cl$_2$, dimethylformamide and ethanol, moderately soluble in toluene, and insoluble in hexanes.

[HOSiPcOSi(CH$_3$)$_2$(CH$_2$)$_3$NH(CH$_3$)$_2$]$^+$[4-C$_9$H$_{19}$C$_6$H$_4$-1-(OCH$_2$CH$_2$)$_{\sim 20}$O(CH$_2$)$_3$SO$_3$]$^-$, Pc 245, Compound 18. A solution of Pc 4 (6.8 mg, 0.0095 mmol), an aqueous solution of acid compound 19 (0.076 mM, 125 µL, ~0.0095 mmol) and ethanol (5 mL) was stirred for 30 min and evaporated to dryness by rotary evaporation (room temperature). The solid was chromatographed (Biobeads, S-X3, CH$_2$Cl$_2$), air dried (room temperature), and weighed (16 mg, ~0.0083 mmol, 87%). UV-vis (CH$_2$Cl$_2$) $\lambda_{max}$, nm (log $\epsilon$): 676 (5.4). NMR (CDCl$_3$): δ 9.35 (m, 8H, 1, 4-Pc H), 8.27 (m, 8H, 2, 3-Pc H), 7.18 (m, 2H, 2,6-C$_6$H$_4$ H), 6.80 (m, 2H, 3,5-C$_6$H$_4$ H), 3.83 (d, H, SO$_3$CH$_2$), 3.63 (m, 80H, C$_9$H$_{19}$C$_6$H$_4$(OCH$_2$CH$_2$)$_{\sim 20}$O(CH$_2$)$_3$SO$_3$), 2.60 (m, 2H, SO$_3$CH$_2$CH$_2$), 1.80 (s, 6H, NCH$_3$). 1.21 (m, 19H, C$_9$H$_{19}$C$_6$H$_4$(OCH$_2$CH$_2$)$_{\sim 20}$O(CH$_2$)$_3$SO$_3$; m, 2H, SiCH$_2$CH$_2$CH$_2$), −1.20 (m, 2H, SiCH$_2$CH$_2$), −2.35 (t, 2H, SiCH$_2$), −2.97 (s, 6H, SiCH$_3$).

Compound 18 is viscous blue oil. It is soluble in CH$_2$Cl$_2$, dimethylformamide and ethanol, moderately soluble in toluene, and insoluble in hexanes.

H(OCH$_2$CH$_2$)$_{\sim 9}$OC(O)(CH$_2$)$_2$C(O)OH, Compound 19. A solution of H(OCH$_2$CH$_2$)$_{\sim 9}$OH (mol wt 400, 420 mg, 1.05 mmol, Aldrich), scuccinyl chloride (325 mg, 2.73 mmol), and CH$_2$Cl$_2$ (5 mL) was stirred at 0° C. for 5 h, added water (1 mL), evaporated to dryness by rotary evaporation (room temperature). The solid was chromatographed (Biobeads, S-X3, CH$_2$Cl$_2$), air dried (room temperature) and weighed (240 mg, ~0.497 mmol, 50% yield). NMR (CDCl$_3$): δ 4.26 (t, 2H, H(OCH$_2$CH$_2$)$_8$OCH$_2$CH$_2$OC(O)(CH$_2$)$_2$C(O)O)), 3.65 (m, 34H, H(OCH$_2$CH$_2$)$_8$OCH$_2$CH$_{20}$C(O)(CH$_2$)$_2$C(O)O)), 2.62 (m, 4H, C(O)OCH$_2$CH$_2$).

Compound 19 is colorless viscous oil. It is soluble in CH$_2$Cl$_2$, dimethylformamide and ethanol, moderately soluble in toluene, and insoluble in hexanes.

[HOSiPcOSi(CH$_3$)$_2$(CH$_2$)$_3$NH(CH$_3$)$_2$]$^+$[H(OCH$_2$CH$_2$)$_9$OC(O)(CH$_2$)$_2$C(O)O]$^-$, Pc 246, Compound 20. A solution of Pc 4 (5.3 mg, 0.0074 mmol), acid 21 (4.6 mg, 0.0074 mmol) and CH$_2$Cl$_2$ (5 mL) was stirred for 30 min and evaporated to dryness by rotary evaporation (room temperature). The solid was chromatographed (Biobeads, S-X3, CH$_2$Cl$_2$), air dried (room temperature) and weighed (5.1 mg, 0.0038 mmol, 52%). UV-vis (CH$_2$Cl$_2$) $\lambda_{max}$, nm (log $\epsilon$): 674 (5.4). NMR (CDCl$_3$): δ 9.31 (m, 8H, 1, 4-Pc H), 8.28 (m, 8H, 2, 3-Pc H), 4.24 (t, 2H, H(OCH$_2$CH$_2$)$_8$OCH$_2$CH$_2$OC(O)(CH$_2$)$_2$C(O)O)), 3.65 (m, 34H, H(OCH$_2$CH$_2$)$_8$OCH$_2$CH$_2$OC(O)(CH$_2$)$_2$C(O)O)), 2.64 (m, 4H, C(O)OCH$_2$CH$_2$), 1.92 (s, 6H, NCH$_3$), 1.21 (t, 2H, SiCH$_2$CH$_2$CH$_2$), −1.09 (m, 2H, SiCH$_2$CH$_2$), −2.30 (t, 2H, SiCH$_2$), −2.96 (s, 6H, SiCH$_3$).

Compound 20 is blue solid. It is soluble in CH$_2$Cl$_2$, dimethylformamide and ethanol, moderately soluble in toluene, and insoluble in hexanes.

H(OCH$_2$CH$_2$)$_{\sim76}$OOC(CH$_2$)$_2$COOH, Compound 21. A solution of H(OCH$_2$CH$_2$)$_{\sim76}$OH (mol wt 3350, 1.06 g, ~0.316 mmol, Aldrich), scuccinyl chloride (90 mg, 0.76 mmol), and CH$_2$Cl$_2$ (5 mL) was stirred at 0° C. for 12 hours, added water (1 mL) and evaporated to dryness by rotary evaporation (room temperature). The solid was chromatographed (Biobeads, S-X3, CH$_2$Cl$_2$), vacuum dried (room temperature) and weighed (922 mg, ~0.291mmol, 92% yield). NMR (CDCl$_3$): 4.24 (t, 2H, H(OCH$_2$CH$_2$)$_{\sim75}$OCH$_2$CH$_2$OC(O)(CH$_2$)$_2$C(O)O)), 3.66 (m, 302H, H(OCH$_2$CH$_2$)$_{\sim75}$OCH$_2$CH$_2$OC(O)(CH$_2$)$_2$C(O)O)), 2.60 (m, 4H, C(O)OCH$_2$CH$_2$), 2.56 (m, 2H, C(O)OCH$_2$CH$_2$).

Compound 21 is white solid. It is soluble in CH$_2$Cl$_2$, dimethylformamide and ethanol, moderately soluble in toluene, and insoluble in hexanes.

[HOSiPcOSi(CH$_3$)$_2$(CH$_2$)$_3$NH(CH$_3$)$_2$]$^+$[H(OCH$_2$CH$_2$)$_{\sim76}$O(O)C(CH$_2$)$_2$C(O)O]$^-$, Pc 247, Compound 22. A solution of Pc 4 (6.8 mg, ~0.0095 mmol), acid compound 23 (40 mg, 0.011 mmol) and CH$_2$Cl$_2$ (5 mL) was stirred for 2 hours and evaporated to dryness by rotary evaporation (room temperature). The solid was chromatographed (Biobeads, S-X3, CH$_2$Cl$_2$), air dried (room temperature), and weighed (15.8 mg, 0.00381 mmol, 40%). UV-vis (CH$_2$Cl$_2$) $\lambda_{max}$ nm (log $\epsilon$): 673 (5.4). NMR (CDCl$_3$): δ 9.40 (m, 8H, 1, 4-Pc H), 8.30 (m, 8H, 2, 3-Pc H), 4.24 (t, 2H, H(OCH$_2$CH$_2$)$_{\sim75}$OCH$_2$CH$_2$OC(O)(CH$_2$)$_2$C(O)O)), 3.64 (m, 203H, H(OCH$_2$CH$_2$)$_{\sim75}$OCH$_2$CH$_2$OC(O)(CH$_2$)$_2$C(O)O)), 2.62 (m, 2H, C(O)OCH$_2$CH$_2$), 2.58 (m, 2H, C(O)OCH$_2$CH$_2$), 1.91 (s, 6H, NCH$_3$), 1.21 (t, 2H, SiCH$_2$CH$_2$CH$_2$), −1.13 (m, 2H, SiCH$_2$CH$_2$), −2.30 (t, 2H, SiCH$_2$), −2.93 (s, 6H, SiCH$_3$).

Compound 22 is blue solid. It is soluble in CH$_2$Cl$_2$, dimethylformamide and ethanol, moderately soluble in toluene, and insoluble in hexanes.

CH$_3$(OCH$_2$CH$_2$)$_{\sim45}$OC(O)(CH$_2$)$_2$C(O)OH, Compound 23. A solution of CH$_3$(OCH$_2$CH$_2$)$_{\sim45}$OH (mol wt 2000, 1.01 g, ~0.505 mmol, Aldrich), succinyl chloride (70 mg, 0.59 mmol), and CH$_2$Cl$_2$ (5 mL) was stirred for 12 hours, added water (1 mL) and evaporated to dryness by rotary evaporation (room temperature). The solid was chromatographed (Biobeads, S-X3, CH$_2$Cl$_2$), vacuum dried (room temperature) and weighed (552 mg, 0.253 mmol, 50% yield). NMR (CDCl$_3$): 4.24 (t, 2H, CH$_3$(OCH$_2$CH$_2$)$_{\sim44}$OCH$_2$CH$_2$OC(O)(CH$_2$)$_2$C(O)O), 3.66 (m, 178H, CH$_3$(OCH$_2$CH$_2$)$_{\sim44}$OCH$_2$CH$_2$OC(O)(CH$_2$)$_2$C(O)O), 3.40 (s, 3H, CH$_3$(OCH$_2$CH$_2$)$_{\sim45}$OC(O)(CH$_2$)$_2$C(O)O), 2.58 (d, H, C(O)OCH$_2$), 2.48 (m, 2H, C(O)OCH$_2$CH$_2$).

Compound 23 is white solid. It is soluble in CH$_2$Cl$_2$, dimethylformamide and ethanol, moderately soluble in toluene, and insoluble in hexanes.

[HOSiPcOSi(CH$_3$)$_2$(CH$_2$)$_3$NH(CH$_3$)$_2$]$^+$[CH$_3$(OCH$_2$CH$_2$)$_{\sim45}$OC(O)(CH$_2$)$_2$C(O)O]$^-$, Pc 248, Compound 24. A solution of Pc 4 (5.6 mg, 0.0078 mmol), acid 25 (17.5 mg, ~0.00845 mmol) and CH$_2$Cl$_2$ (5 mL) was stirred for 40 min and evaporated to dryness by rotary evaporation (room temperature). The solid was chromatographed (Biobeads, S-X3, CH$_2$Cl$_2$), air dried (room temperature), and weighed (15.8 mg, 0.00581 mmol, 75%). UV-vis (CH$_2$Cl$_2$) $\lambda_{max}$, nm (log $\epsilon$): 673 (5.4). NMR (CDCl$_3$): δ 9.41 (m, 8H, 1, 4-Pc H), 8.30 (m, 8H, 2, 3-Pc H), 4.23 (t, 2H, CH$_3$(OCH$_2$CH$_2$)$_{\sim44}$OCH$_2$CH$_2$OC(O)(CH$_2$)$_2$C(O)O), 3.63 (m, 178H, CH$_3$(OCH$_2$CH$_2$)$_{\sim44}$OCH$_2$CH$_2$OC(O)(CH$_2$)$_2$C(O)O), 3.38 (s, 3H, CH$_3$(OCH$_2$CH$_2$)$_{\sim45}$OC(O)(CH$_2$)$_2$C(O)O), 2.59 (d, 2H, C(O)OCH$_2$), 2.53 (m, 2H, C(O)OCH$_2$CH$_2$), 1.81 (s, 6H, NCH$_3$), 1.09 (t, 2H, SiCH$_2$CH$_2$CH$_2$), −1.17 (m, 2H, SiCH$_2$CH$_2$), −2.31 (t, 2H, SiCH$_2$), −2.94 (s, 6H, SiCH$_3$).

Compound 24 is blue solid. It is soluble in CH$_2$Cl$_2$, dimethylformamide and ethanol, moderately soluble in toluene, and insoluble in hexanes.

[HOSiPcOSi(CH$_3$)$_2$(CH$_2$)$_3$NH(CH$_3$)$_2$]$^+$ [C$_4$H$_3$N$_4$OC$_4$H$_6$O$_3$CH$_2$OPO$_3$H]$^-$, Pc 249, Compound 25. A solution of Pc 4 (13 mg, 0.018 mmol), an aqueous solution of inosinic acid (Aldrich, 0.012 M, 1.5 mL, 0.018 mmol) and tetrahydrofuran (20 mL) was stirred for 5 min and evaporated to dryness by rotary evaporation (room temperature). The solid was chromatographed (Biobeads, S-X3, CH$_2$Cl$_2$), air dried (room temperature) and weighed (7.2 mg, 0.0070 mmol, 39%). UV-vis (DMSO) $\lambda_{max}$, nm (log $\epsilon$): 672 (5.4). NMR (DMSO): δ 9.64 (m, 8H, 1, 4-Pc H), 8.46 (m, 8H, 2, 3-Pc H), 8.33 (s, 1H, h-8 H), 8.03 (m, 1H, h-2 H), 4.14 (t, 1H, f-2' H), 3.99 (t, 1H, f-3' H), 3.79 (t, 1H, f-4 H), 3.58 (d, 2H, f-5' H), 1.81 (s, 6H, NCH$_3$), 1.22 (t, 2H, SiCH$_2$CH$_2$CH$_2$), −1.18 (m, 2H, SiCH$_2$CH$_2$), −2.33 (t, 2H, SiCH$_2$), −2.96 (s, 6H, SiCH$_3$).

Compound 25 is blue solid. It is soluble in CH$_2$Cl$_2$, dimethylformamide and ethanol, moderately soluble in toluene, and insoluble in hexanes.

[HOSiPcOSi(CH$_3$)$_2$(CH$_2$)$_3$NH(CH$_3$)$_2$]$^+$[CH$_3$SO$_3$]$^-$, Pc 250, Compound 26. A suspension of Pc 4 (11 mg, 0.015 mmol), methanesulfonic acid (1.1 μL, 0.015 mmol) and toluene (20 mL) was stirred for 30 min and evaporated to dryness by rotary evaporation (room temperature). The solid was chromatographed (Biobeads, S-X3, CH$_2$Cl$_2$), air dried (room temperature) and weighed (6.8 mg, 0.0084 mmol, 56%). UV-vis (CH$_2$Cl$_2$) $\lambda_{max}$, nm (log $\epsilon$): 672 (5.4). NMR (CDCl$_3$): δ 9.32 (m, 8H, 1, 4-Pc H), 8.28 (m, 8H, 2, 3-Pc H), 2.43 (d, 3H, SO$_3$CH$_3$), 1.94 (d, 6H, NCH$_3$), 1.20 (t, 2H, SiCH$_2$CH$_2$CH$_2$), −1.15 (m, 2H, SiCH$_2$CH$_2$), −2.29 (t, 2H, SiCH$_2$), −2.96 (s, 6H, SiCH$_3$).

Compound 26 is blue solid. It is soluble in CH$_2$Cl$_2$, dimethylformamide and ethanol, moderately soluble in toluene, and insoluble in hexanes.

[HOSiPcOSi(CH$_3$)$_2$(CH$_2$)$_3$NH(CH$_3$)$_2$]$^+$[NaSO$_4$]$^-$, Pc 251, Compound 27. A suspension of Pc 4 (10 mg, 0.014 mmol), aqueous NaHSO$_4$ (0.012 M, 1.2 mL, 0.014 mmol) and tetrahydrofuran (20 mL) was stirred for 5 min and evaporated to dryness by rotary evaporation (room temperature). The solid was chromatographed (Biobeads, S-X3, CH$_2$Cl$_2$), air dried (room temperature) and weighed (6.0 mg, 0.0070 mmol, 50%). UV-vis (CH$_2$Cl$_2$) $\lambda_{max}$, nm (log $\epsilon$): 672 (5.4). NMR (CDCl$_3$): δ 9.31 (m, 8H, 1, 4-Pc H), 8.28 (m, 8H, 2, 3Pc H), 1.85 (s, 6H, NCH$_3$), 1.18 (t, 2H, SiCH$_2$CH$_2$CH$_2$), −1.19 (m, 2H, SiCH$_2$CH$_2$), −2.34 (t, 2H, SiCH$_2$), −2.97 (s, 6H, SiCH$_3$).

Compound 27 is blue solid. It is soluble in CH$_2$Cl$_2$, dimethylformamide and ethanol, moderately soluble in toluene, and insoluble in hexanes.

Example 3

Syntheses of OH-Replaced Derivative Salts

[ClSiPcOSi(CH$_3$)$_2$(CH$_2$)$_3$NH(CH$_3$)$_2$]$^+$Cl$^-$, Pc 230, Compound 28. Under Ar, a suspension of Pc 4 (12 mg, 0.017 mmol), toluene (1 mL) and 2,6-di-tert-butyl-pyridine (8 μL) was treated dropwise with a solution of SOCl$_2$ (2.5 μl, 0.034 mmol) and toluene (0.5 mL), stirred for 1 hour, and filtered. The filtrate was carefully vacuum dried (room temperature) and weighed (4 mg, 0.005 mmol, 16%). UV-vis(CH$_2$Cl$_2$) $\lambda_{max}$, nm (log $\epsilon$): 670 (5.4). NMR (CDCl$_3$): δ 9.68 (m, 8H, 1, 4-Pc H), 8.41 (m, 8H, 2, 3-Pc H), 2.07 (d, 6H, NCH$_3$), 1.41 (t, 2H, SiCH$_2$CH$_2$CH$_2$), −0.79 (m, 2H, SiCH$_2$CH$_2$), −2.08 (t, 2H, SiCH$_2$), −2.69 (s, 6H, SiCH$_3$).

Compound 28 is a blue solid. It is soluble in $CH_2Cl_2$, dimethylformamide and ethanol, moderately soluble in toluene, and insoluble in hexanes. Compound 28 is hydrolyzed by air to Pc 4 with 30 min.

[$CH_3C(O)C(O)OSiPcOSi(CH_3)_2(CH_2)_3NH(CH_3)_2$]$^+Cl^-$, Pc 188, Compound 29. Under Ar, a solution of pyruvic acid (0.8 g, 0.009 mol), $SO_2Cl_2$ (2.0 g, 0.017 mol) and $CH_2Cl_2$ (3 mL) was stirred for 30 minutes, and concentrated by rotary evaporation (room temperature). The concentrate was mixed with Pc 4 (19 mg, 0.026 mmol) and $CH_2Cl_2$ (5 mL), and the mixture was stirred for 50 minutes and evaporated to dryness by rotary evaporation (room temperature). The solid was dried ($10^{-2}$ Torr, 100° C.), dissolved in $CH_2Cl_2$ (0.1 mL), reprecipitated with toluene, recovered by filtration, vacuum dried, and weighed (12 mg, 0.015 mmol, 58% from Pc 4). UV-vis ($CH_2Cl_2$) $\lambda_{max}$, nm (log ε): 672 (5.4). NMR ($CDCl_3$): δ 9.67 (m, 8H, 1, 4-Pc H), 8.39 (m, 8H, 2, 3-Pc H), 2.08 (s, 3H, $OCOCOCH_3$), 1.95 (s, 6H, $NCH_3$), 1.42 (t, 2H, $SiCH_2CH_2CH_2$), −0.99 (m, 2H, $SiCH_2CH_2$), −2.15 (t, 2H, $SiCH_2$), −2.75 (s, 6H, $SiCH_3$).

Compound 29 is a blue solid. It is soluble in $CH_2Cl_2$, dimethylformamide and ethanol, moderately soluble in toluene, and insoluble in hexanes. Compound 29 is hydrolyzed by air to Pc 4 with 2 h.

Example 4

Solubility of Pc 4, OH-Replaced Derivatives of Pc 4, Salts of Pc 4 and OH-Replaced Derivatives of Pc 4 in Their Salt Form The qualitative solubilities of Pc 4, the OH-replaced derivatives of Pc 4, the salts of Pc 4, and the OH-replaced derivatives of Pc 4 in their salt form were determined in six representative solvents: $CH_2Cl_2$, dimethylformamide, ethanol, acetonitrile, toluene, and hexanes. The solubilities of Pc 4 and its OH-replaced derivatives in the six solvents are very similar. These compounds are at least moderately soluble in $CH_2Cl_2$, dimethylformamide, ethanol, and toluene. The lack of good solubility of the OH-replaced derivatives in toluene is attributed in part to the lack of multiple, flexible, aromatic ring-containing groups in the ligands. The solubilities of the salts and the OH-replaced derivative-salts in the six solvents are also very similar to one another. They are soluble in the same four solvents that Pc 4 and the OH-replaced derivatives are.

The quantitative solubilities of Pc 4, OH-replaced derivatives of Pc 4, selected Pc 4 salts, and selected OH-replaced derivative salts were determined in various aqueous dispersants. Disperstants are agents added to an aqueous solution to prevent clumping, and include a number of surfactant and surfactant-like molecules. The concentration of Pc 4 was determined in $H_2O$, and in Tween 80 (polyoxyethylene (20) sorbitan monooleate), povidone (polyvinyl pyrrolidone), Dow Corning 193, potassium poly(ethylene glycol)-4-nonylphenyl-3-sulfopropyl ether, poly(ethylene glycol) methyl ether 2000, and 1,6-hexanediol at a dispersant concentration of 7.2 mg/mL, as shown in Table 4. The concentration of Pc 4 in the dispersant solutions is higher than its concentration in water. In the dispersant solutions, its concentration varies by more than 100-fold—from 0.050 μM in poly(ethylene glycol) methyl ether 2000 to 7.1 μM in Tween 80. The variation of its concentration in the dispersant solutions is likely caused by the fact that dispersants differ greatly in structure and molecular weight, and thus their interactions with Pc 4 can be expected to be very different.

TABLE 4

Concentration of Pc 4 in $H_2O$ and in Aqueous Dispersants

| | | dispersant | | Pc 4 conc | |
| | | | conc | | |
| name | formula | (mg/mL) | (mM) | (μg/mL) | (μM) |
| --- | --- | --- | --- | --- | --- |
| none | none | 0.0 | 0.0 | 0.0 | 0.0 |
| Tween 80 | 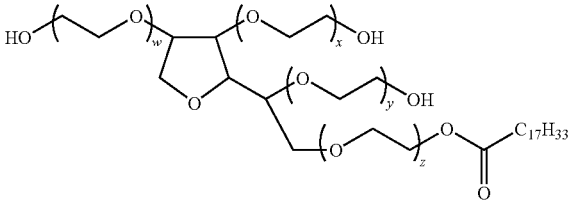 w + x + y + z = 20 | 7.2 | 5.5 | 5.1 | 7.1 |
| povidone | 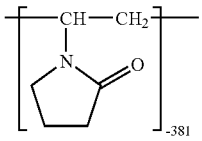 | 7.2 | 0.18 | 0.09 | 0.12 |
| Dow Corning 193 | 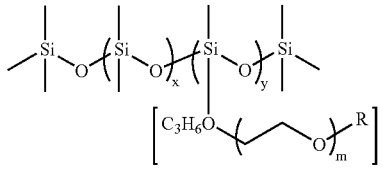 | 7.2 | — | 0.29 | 0.40 |

TABLE 4-continued

Concentration of Pc 4 in H₂O and in Aqueous Dispersants

| name | formula | dispersant conc (mg/mL) | (mM) | Pc 4 conc (µg/mL) | (µM) |
|---|---|---|---|---|---|
| potassium poly(ethylene glycol)-4-nonylphenyl-3-sulfopropyl ether | KO-SO₂-(CH₂)₃-(OCH₂CH₂)₂₀-O-C₆H₄-(C₈H₁₇) | 7.2 | 5.7 | 4.3 | 6.0 |
| poly(ethylene glycol)methyl ether 2000 | H-(OCH₂CH₂)₄₅-O- | 7.2 | 3.6 | 0.036 | 0.050 |
| 1,6-hexanediol | HO-(CH₂)₆-OH | 7.2 | 61 | 7.2 | 10 |

The concentrations of the OH-replaced derivatives were determined in Tween 80 at a dispersant concentration of 7.2 mg/mL. The concentrations of the derivatives were moderate (~20 mg/mL) to good (~30 mg/mL). The concentrations of the salts in Tween 80 at a concentration of 7.2 mg/mL are much higher than the concentration of Pc 4 in Tween 80 at 7.2 mg/mL, as shown in Table 5. As can be seen, the concentrations range from 1 µM for stearate compound 8 to 874 µM for sulfonate compound 18. Clearly Tween 80 at 7.2 mg/mL is a good dispersant for the salts. The high concentration of sulfonate compound 18 in Tween 80 is attributable in part to the presence of polyethylene glycol chains in both sulfonate compound 18 and Tween 80. Taken as a whole, the data in Table 5 make it clear that the structure of the salt anion is very important. This is consistent with the idea that specific types of anion-dispersant interaction should be very important.

TABLE 5

Concentrations of Salts in Dilute Aqueous Tween 80

| | salt anion name | dispersant conc (mg/mL) | (mM) | salt conc (µg/mL) | (µM) |
|---|---|---|---|---|---|
| Pc 4 | none | 7.2 | 5.5 | 5.1 | 7.1 |
| 5 Pc 234 | chloride | 7.2 | 5.5 | 79 | 110 |
| 27 Pc 251 | bisulfate | 7.2 | 5.5 | 55 | 77 |
| 26 Pc 250 | methanesulfonate | 7.2 | 5.5 | 209 | 262 |
| 18 Pc 245 | sulfonate | 7.2 | 5.5 | 630 | 874 |
| 14 Pc 242 | sulforhodamine B ate | 7.2 | 5.5 | 112 | 89 |
| 13 Pc 241 | dimethylphosphinate | 7.2 | 5.5 | 362 | 455 |
| 25 Pc 249 | inosinate | 7.2 | 5.5 | 196 | 274 |
| 15 Pc 243 | lactate | 7.2 | 5.5 | 24 | 33 |
| 7 Pc 235 | succinate | 7.2 | 5.5 | 43 | 53 |
| 20 Pc 246 | polyethylene glycol succinate | 7.2 | 5.5 | 101 | 141 |
| 24 Pc 248 | polyethylene glycol methyl ether succinate | 7.2 | 5.5 | 70 | 98 |
| 22 Pc 247 | polyethylene glycol succinate | 7.2 | 5.5 | 104 | 146 |
| 11 Pc 239 | (+)-α-tocopherol succinate | 7.2 | 5.5 | 5 | 4 |
| 6 Pc 229 | malate | 7.2 | 5.5 | 118 | 165 |
| 8 Pc 236 | stearate | 7.2 | 5.5 | 1 | 1 |
| 12 Pc 240 | oleate | 7.2 | 5.5 | 2 | 2 |
| 9 Pc 237 | salicylate | 7.2 | 5.5 | 24 | 29 |
| 10 Pc 238 | acetylsalicylate | 7.2 | 5.5 | 21 | 23 |
| 14 Pc 244 | polydimethyl siloxane decanoate | 7.2 | 5.5 | 232 | 23 |

The concentration of sulfonate salt 18 in various dispersants at a dispersant concentration of 7.2 mg/mL varies over an extremely wide range −0.031 µM for polyethylene glycol monomethyl ether 750 to 1418 µM for potassium poly(ethylene glycol)-4-nonylphenyl-3-sulfopropyl ether (about 50,000-fold), as shown in Table 6. From the results for the sulfopropyl ether as a dispersant, it is apparent that it can be an excellent dispersant for phthalocyanine salts. Its ability to function so effectively with sulfonate compound 18 is attributable to the identity of the anion in it and the anion in sulfonate compound 18. Because none of the polyethylene glycol monomethyl ethers are nearly as good dispersants, it also is clear that the polarity of potassium poly(ethylene glycol)-4-nonylphenyl-3-sulfopropyl ether is an important contributor to its effectiveness as a dispersant for sulfonate compound 18. Finally, it is clear that the structure of a dispersant is very important.

TABLE 6

Concentration of Sulfonate 18 in Aqueous Dispersants

| | | salt anion | | dispersant | | conc | | salt conc | |
|---|---|---|---|---|---|---|---|---|---|
| | | name | formula | name | formula | (mg/mL) | (mM) | (µg/mL) | (µM) |
| 18 | Pc 245 | sulfonate | | Tween 80 | | 7.2 | 5.5 | 630 | 874 |
| | | | | povidone | [−CH−CH$_2$−]$_n$ with pyrrolidinone ring on N | 7.2 | 0.18 | 14 | 19 |
| | | | | PEG methyl ether 350 | H−O−(CH$_2$CH$_2$O)$_{-7}$− | 7.2 | 21 | 9.3 | 13 |
| | | | | PEG methyl ether 750 | H−O−(CH$_2$CH$_2$O)$_{-16}$− | 7.2 | 9.6 | 0.022 | 0.031 |
| | | | | PEG methyl ether 2000 | H−O−(CH$_2$CH$_2$O)$_{-45}$− | 7.2 | 3.6 | 1.3 | 1.8 |
| | | | | PEG methyl ether 5000 | H−O−(CH$_2$CH$_2$O)$_{-112}$− | 7.2 | 1.4 | 3.4 | 4.8 |
| | | | | Dow Corning 193 | Si−O−(Si−O)$_x$−(Si−O)$_y$−Si with [C$_3$H$_6$O−(O)$_m$−R] | 7.2 | | 50 | 70 |
| | | | | potassium poly(ethylene glycol)-4-nonylphenyl-3-sulfopropyl ether | KO−S(O)$_2$−(CH$_2$)$_3$−(O−CH$_2$CH$_2$)$_{-20}$−O−C$_6$H$_4$−(C$_9$H$_{19}$) | 7.2 | 5.0 | ~1018 | ~1418 |

In summary, a survey of the salt-dispersant data indicates that, povidone is not a good salt dispersant (sulfonate compound 18, Data not shown), whereas Tween 80 is a good salt dispersant (sulfonate compound 18, Table 6).

As stated above, the salt results in which the dispersant is constant and the salt anion is varied, Table 5, show that salt anion structure is very important. Similarly, the salt results where the salt anion is constant and the dispersant is varied, (data not shown) show that the dispersant structure is very important. Finally, the salt results where the dispersant and the salt anion are constant and the dispersant concentration is varied (Table 6) demonstrate that dispersant concentration can be very important.

Example 5

Synthesis of Phthalocyanines with Polyunsaturated Ester Ligands and Polyunsaturated Anions Ester Synthesis Stearate Ester of SiPc(OH)$_2$, SiPc[OC(O)(CH$_2$)$_{17}$]$_2$. Under Ar, a mixture of SiPc(OH)$_2$ (13 mg, 0.02 mmol) and stearic acid (105 mg, 0.37 mmol) was stirred at 130° C. for 3 hr, diluted with CH$_2$Cl$_2$ (5 mL) and filtered. The filtrate was evaporated to dryness by rotary evaporation (room temperature), and the solid was chromatographed (neutral Al$_2$O$_3$ (III), CH$_2$Cl$_2$), washed (CH$_3$CN), vacuum dried (room temperature), and weighed (11 mg, 50%).

Linoleate Ester of SiPc(OH)$_2$, SiPc(OC(O)(CH$_2$)$_6$(CH$_2$CH=CH)$_2$(CH$_2$)$_4$CH$_3$]$_2$. Under Ar, a mixture of SiPc(OH)$_2$ (20 mg, 0.03 mmol) and linoleic acid (0.1 mL, 0.32 mmol) was stirred at 130° C. for 3 hours, diluted with CH$_2$Cl$_2$ (5 mL) and filtered. The filtrate was evaporated to dryness by rotary evaporation (room temperature), and the solid was chromatographed (neutral Al$_2$O$_3$ (III), CH$_2$Cl$_2$), washed (CH$_3$CN), vacuum dried (room temperature), and weighed (17 mg, 50%).

Linolenate Ester of SiPc(OH)$_2$, SiPc(OC(O)(CH$_2$)$_6$(CH$_2$CH=CH)$_3$CH$_2$CH$_3$]$_2$. Under Ar, a mixture of SiPc(OH)$_2$ (20 mg, 0.03 mmol) and linolenic acid (0.1 mL, 0.32 mmol) was stirred at 130° C. for 3 hours, diluted with CH$_2$Cl$_2$ (5 mL) and filtered. The filtrate was evaporated to dryness by rotary evaporation (room temperature), and the solid was chromatographed (neutral Al$_2$O$_3$ (III), CH$_2$Cl$_2$), washed (CH$_3$CN), vacuum dried (room temperature), and weighed (12 mg, 38%).

Salt Synthesis

Linoleate Salt of Pc 12, {SiPc[OSi(CH$_3$)$_2$(CH$_2$)$_3$NH(CH$_3$)$_2$]$_2$}$^{2+}$[CH$_3$(CH$_2$)$_4$(CH=CHCH$_2$)$_2$(CH$_2$)$_6$COO$^-$]$_2$.

Under Ar, a solution of Pc 12, SiPc[OSi(CH₃)₂(CH₂)₃N(CH₃)₂]₂, (5.0 mg, 0.0058 mmol), linoleic acid (3.2 mg, 0.011 mmol) and CH₂Cl₂ (5 mL) was stirred for 30 min and evaporated to dryness by rotary evaporation (room temperature). The solid was chromatographed (Biobeads, S-X3, CH₂Cl₂), vacuum dried (room temperature), and weighed (6.0 mg, 73%).

Linolenate Salt of Pc 12, {SiPc[OSi(CH₃)₂(CH₂)₃NH(CH₃)₂]₂}²⁺[CH₃CH₂(CH=CHCH₂)₃(CH₂)₆COO⁻]₂.
Under Ar, a solution of Pc 12, SiPc[OSi(CH₃)₂(CH₂)₃N(CH₃)₂]₂, (7.3 mg, 0.0085 mmol), linolenic acid (4.7 mg, 0.017 mmol) and CH₂Cl₂ (5 mL) was stirred for 30 min and evaporated to dryness by rotary evaporation (room temperature). The solid was chromatographed (Biobeads, S-X3, CH₂Cl₂), vacuum dried (room temperature), and weighed (9.0 mg, 75%).

cis-4,7,10,13,16,19-Docosahexaenoate Salt of Pc 12, DHAate Salt of Pc 12, {SiPc[OSi(CH₃)₂(CH₂)₃NH(CH₃)₂]₂}²⁺[CH₃CH₂(CH=CHCH₂)₆CH₂COO⁻]₂. Under Ar, a solution of Pc 12, SiPc[OSi(CH₃)₂(CH₂)₃N(CH₃)₂]₂, (3.3 mg, 0.0038 mmol), cis-4,7,10,13,16,19-docosahexaenoic acid (CH₃CH₂(CH=CHCH₂)₆CH₂COOH) (2.5mg, 0.0076 mmol) and CH₂Cl₂ (5 mL) was stirred for 30 min under Ar and evaporated to dryness by rotary evaporation (room temperature). The solid was chromatographed (Biobeads, S-X3, CH₂Cl₂), vacuum dried (room temperature), and weighed (3.7 mg, 64%)

Example 6

Photofading of Phthalocyanines with Polyunsaturated Ester Ligands and Polyunsaturated Anions Linolenate Ester of SiPc(OH)₂, SiPc(OC(O)(CH₂)₆(CH₂CH=CH)₃CH₂CH₃]₂. A solution of the linolenate ester of SiPc(OH)₂ in toluene (~0.01 mM) in a capped quartz cuvette was irradiated at room temperature with light from a tungsten lamp (300 W) in a projector (Kodak EKTAGRAPHIC III E, Kodak, Japan) with a lamp-to-cuvette separation of 30 cm. The UV-vis absorption of the solution at 684 nm was taken periodically and the percent ester remaining was calculated.

The photofading of other esters and the salts was determined in a like manner, as shown in Table 7 and FIG. 1. The compounds below Table 7 show phthalocyanines with (a) polyunsaturated ester ligands and (b) with polyunsaturated anions

TABLE 7

| | Photofading of Phthalocyanines | | | | |
|---|---|---|---|---|---|
| acid | | ester[a] | | salt[b] | |
| name | structure | hrs | % left | hrs | % left |
| stearic | HOOC⌇⌇⌇⌇⌇⌇ | 20 | 100 | | |
| oleic | HOOC⌇⌇⌇=⌇⌇⌇ | 20 | 93 | | |
| linoleic | HOOC⌇⌇⌇=⌇=⌇⌇ | 4 | 95 | | |
| | | 12 | 95 | | |
| | | 20 | 94 | | |
| linolenic | HOOC⌇⌇⌇=⌇=⌇=⌇ | 4 | 88 | 12 | 79 |
| | | 12 | 68 | 20 | 73 |
| | | 20 | 59 | | |
| DHA | HOOC⌇=⌇=⌇=⌇=⌇=⌇=⌇ | 4 | 13 | 4 | 72 |
| | | 8 | 6 | 8 | 62 |

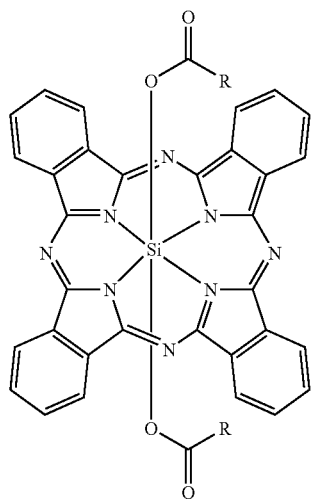

TABLE 7-continued

Photofading of Phthalocyanines

| | | acid | ester[a] | | salt[b] | |
|---|---|---|---|---|---|---|
| name | structure | | hrs | % left | hrs | % left |

[b]

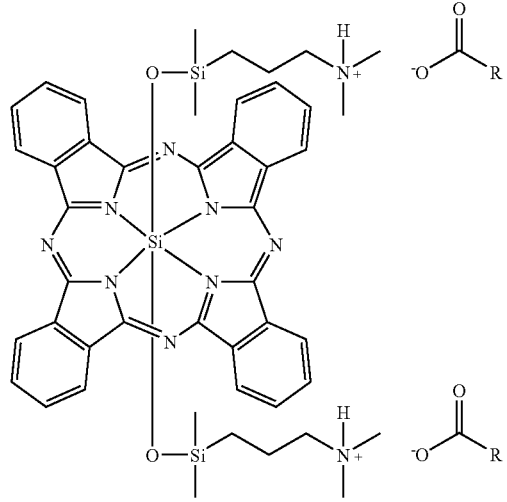

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

The invention claimed is:

1. A phthalocyanine polyunsaturated fatty acid salt, with a structure according to formula (1):

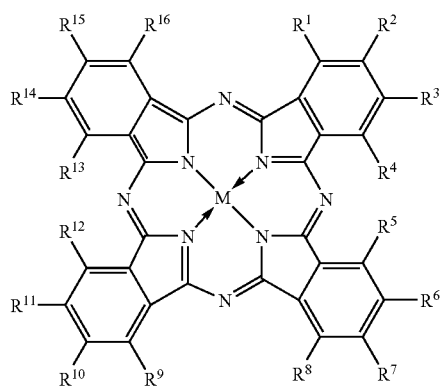

(I)

wherein M is $(R')_e X[OSi(CH_3)_2(CH_2)_a N^+(R'')_b(R''')_c Y^-]_d$;

X is selected from Si or Al;

R' is selected from OH, $CH_3$, halogen, $OCH_3$, $OC(O)CH_3$, and $OC(O)CH_2CH_3$;

R'' is selected from H, $CH_3$, $C_2H_5$, $C_4H_9$, $C_4H_8NH$, $C_4H_8N$, $C_4H_8NCH_3$, $C_4H_8S$, $C_4H_8O$, $OC(O)CH_3$, $OC(O)$, CS, CO, OH, $C_4H_8N(CH_2)_3CH_3$, $(CH_2)_2N(CH_3)_2$, $(CH_2)_fN((CH_2)_g(CH3))_2$, and an alkyl group having from 1 to 12 carbon atoms;

R''' is selected from H, $CH_3$, $SO_2CH_3$, $(CH_2)_2N(CH_3)_2$, $(CH_2)_{11}CH_3$, $C(S)NHC_6H_{11}O_5$, $(CH_2)_fN((CH_2)_g(CH_3))_2$, and an alkyl group having from 1 to 12 carbon atoms;

Y is a polyunsaturated fatty acid anion;

a is an integer from 2 to 4;

b is an integer from 0 to 3;

c is an integer from 0 to 2;

d is 1 or 2;

e is 0 or 1;

f is an integer from 1 to 12;

g is an integer from 1 to 11;

$R^1$, $R^4$, $R^5$, $R^8$, $R^9$, $R^{12}$, $R^{13}$, and $R^{16}$ are each independently selected from hydrogen, halogen, nitro, cyano, hydroxy, thiol, amino, and methyl; and $R^2$, $R^3$, $R^6$, $R^7$, $R^{10}$, $R^{11}$, $R^{14}$, and $R^{15}$ are each independently selected from hydrogen, halogen, nitro, cyano, hydroxy, thiol, amino, carboxy, aryl, heteroaryl, carbocyclyl, heterocyclyl, $C_{1-6}$alkyl, $C_{1-6}$alkenyl, $C_{1-6}$alkynyl, $C_{1-6}$alkoxy, $C_{1-6}$acyl, $C_{1-6}$alkylcarbonyloxy, $C_{1-6}$carbocyclylalkyl, $C_{1-6}$aminoalkyl, $C_{1-6}$alkylamino, $C_{1-6}$thioalkyl, $C_{1-6}$alkylthio, $C_{1-6}$hydroxyalkyl, $C_{1-6}$alkyloxycarbonyl, $C_{1-6}$alkylaminocarbonyl, and $C_{1-6}$alkylcarbonylamino.

2. The polyunsaturated fatty acid salt of claim 1, wherein d and e of formula (1) are both 1.

3. The polyunsaturated fatty acid salt of claim 1, wherein $R^1$-$R^{16}$ are independently selected from hydrogen, halogen, nitro, cyano, hydroxyl, thiol, amino, and methyl.

4. The polyunsaturated fatty acid salt of claim 1, wherein $R^1$-$R^{16}$ are hydrogen.

5. The polyunsaturated fatty acid salt of claim 1, wherein M is selected from the group consisting of $AlOSi(CH_3)_2(CH_2)_3N^+(CH_3)_2Y^-$; $CH_3SiOSi(CH_3)_2(CH_2)_3N^+(CH_3)_2Y^-$; $HOSiOSi(CH_3)_2(CH_2)_3N^+(CH_3)_2Y^-$; $HOSiOSi(CH_3)_2$ $(CH_2)_4N^+HSO_2CH_3Y^-$; $HOSiOSi(CH_3)_2(CH_2)_3N^+(CH_2CH_3)(CH_2)_2N(CH_3)_2Y^-$; $HOSiOSi(CH_3)_2(CH_2)_3N^+C_4H_8O^-Y^-$; $HOSiOSi(CH_3)_2(CH_2)_4N^+(CH_3)_2Y^-$; $HOSiOSi(CH_3)_2(CH_2)_3N^+C_4H_8SY^-$; $HOSiOSi(CH_3)_2(CH_2)_3N^+(CH_2)_3(CH_3)_2Y^-$; $HOSiOSi(CH_3)_2(CH_2)_3N^+CSY^-$; $HOSiOSi(CH_3)_2(CH_2)_3N^+[(CH_2)_3N(CH_3)_2]_2Y^-$; $HOSiOSi(CH_3)_2(CH_2)_3N^+C_4H_8NCH_3Y^-$; $HOSiOSi(CH_3)_2(CH_2)_3N^+C_4H_8N(CH_2)_3CH_3Y^-$; $FSiOSi(CH_3)_2(CH_2)_3N^+(CH_3)_2Y^-$; $ClSiOSi(CH_3)_2(CH_2)_3N^+(CH_3)_2Y^-$; $CH_3C(O)OSiOSi(CH_3)_2(CH_2)_3N^+(CH_3)_2Y^-$; $CH_3CH_2C(O)OSiOSi(CH_3)_2(CH_2)_3N^+(CH_3)_2Y^-$; and $CH_3OSiOSi(CH_3)_2(CH_2)_3N^+(CH_3)_2Y^-$.

6. The polyunsaturated fatty acid salt of claim 1, wherein M is selected from the group consisting of $HOSiOSi(CH_3)_2(CH_2)_3N^+(CH_3)_2Y^-$; $FSiOSi(CH_3)_2(CH_2)_3N^+(CH_3)_2Y^-$; $ClSiOSi(CH_3)_2(CH_2)_3N^+(CH_3)_2Y^-$; $CH_3C(O)OSiOSi(CH_3)_2(CH_2)_3N^+(CH_3)_2Y^-$; $CH_3CH_2C(O)OSiOSi(CH_3)_2(CH_2)_3N^+(CH_3)_2Y^-$; and $CH_3OSiOSi(CH_3)_2(CH_2)_3N^+(CH_3)_2Y^-$.

7. The polyunsaturated fatty acid salt of claim 1, wherein M is $HOSiOSi(CH_3)_2(CH_2)_3N^+(CH_3)_2Y^-$.

8. The polyunsaturated fatty acid salt of claim 1, wherein the polyunsaturated fatty acid is an omega-3 fatty acid.

9. The polyunsaturated fatty acid salt of claim 8, wherein the polyunsaturated fatty acid is linolenic acid.

10. A phthalocyanine polyunsaturated fatty acid ester, with a structure according to formula (1):

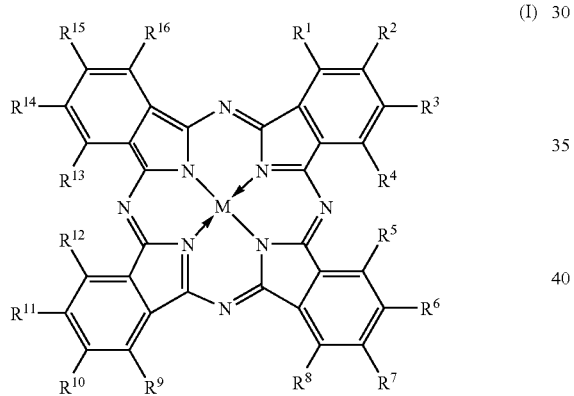

wherein M is $(R')_aX(R'')_e[OSi(CH_3)_2(CH_2)_aN(R''')_b(R'''')_c]_h$;

X is selected from Si or Al;

R' consists of a polyunsaturated fatty acid attached to X through an ester linkage;

R" is selected from $OH$, $CH_3$, halogen, $OCH_3$, $OC(O)CH_3$, and $OC(O)CH_2CH_3$;

R''' is selected from H, $CH_3$, $C_2H_5$, $C_4H_9$, $C_4H_8NH$, $C_4H_8N$, $C_4H_8NCH_3$, $C_4H_8S$, $C_4H_8O$, $OC(O)CH_3$, $OC(O)$, $CS$, $CO$, $OH$, $C_4H_8N(CH_2)_3CH_3$, $(CH_2)_2N(CH_3)_2$, $(CH_2)_fN((CH_2)_g(CH_3))_2$, and an alkyl group having from 1 to 12 carbon atoms;

R"" is selected from H, $CH_3$, $SO_2CH_3$, $(CH_2)_2N(CH_3)_2$, $(CH_2)_{11}CH_3$, $C(S)NHC_6H_{11}O_5$, $(CH_2)_fN((CH_2)_g(CH_3))_2$, and an alkyl group having from 1 to 12 carbon atoms; a is an integer from 2 to 4;

b is an integer from 0 to 3;

c is an integer from 0 to 2;

d is 1 or 2;

e is 0 or 1;

f is an integer from 1 to 12;

g is an integer from 1 to 11;

h is $[2-(d+e)]$)

$R^1$, $R^4$, $R^5$, $R^8$, $R^9$, $R^{12}$, $R^{13}$, and $R^{16}$ are each independently selected from hydrogen, halogen, nitro, cyano, hydroxy, thiol, amino, and methyl; and $R^2$, $R^3$, $R^6$, $R^7$, $R^{10}$, $R^{11}$, $R^{14}$, and $R^{15}$ are each independently selected from hydrogen, halogen, nitro, cyano, hydroxy, thiol, amino, carboxy, aryl, heteroaryl, carbocyclyl, heterocyclyl, $C_{1-6}$alkyl, $C_{1-6}$alkenyl, $C_{1-6}$alkynyl, $C_{1-6}$alkoxy, $C_{1-6}$acyl, $C_{1-6}$alkylcarbonyloxy, $C_{1-6}$carbocyclylalkyl, $C_{1-6}$aminoalkyl, $C_{1-6}$alkylamino, $C_{1-6}$thioalkyl, $C_{1-6}$alkylthio, $C_{1-6}$hydroxyalkyl, $C_{1-6}$alkyloxycarbonyl, $C_{1-6}$alkylaminocarbonyl, and $C_{1-6}$alkylcarbonylamino.

11. The phthalocyanine compound of claim 10, wherein the polyunsaturated fatty acid is an omega-3 fatty acid.

12. The phthalocyanine compound of claim 10, wherein the polyunsaturated fatty acid is linolenic acid.

13. A pharmaceutical composition comprising a phthalocyanine according to claim 1 and a pharmaceutically acceptable carrier.

14. A pharmaceutical composition comprising a phthalocyanine according to claim 10 and a pharmaceutically acceptable carrier.

* * * * *